United States Patent [19]

Osther et al.

[11] Patent Number: 5,529,776
[45] Date of Patent: Jun. 25, 1996

[54] ANTI-HIV-1 NEUTRALIZING ANTIBODIES

[75] Inventors: Kurt B. Osther, Westboro, Mass.; Gottfried H. Kellermann, Osceola, Wis.

[73] Assignee: Verigen Inc., Hopkinton, Mass.

[21] Appl. No.: 174,944

[22] Filed: Dec. 27, 1993

Related U.S. Application Data

[63] Continuation-in-part of Ser. No. 694,586, May 2, 1991, abandoned, which is a continuation-in-part of Ser. No. 376,247, Jul. 6, 1989, abandoned, which is a continuation-in-part of Ser. No. 215,867, Jul. 6, 1988, abandoned.

[51] Int. Cl.$^6$ .......................... A61K 39/42; C07K 16/00
[52] U.S. Cl. ..................... 424/160.1; 530/389.4
[58] Field of Search ................. 424/160.1; 530/389.4

[56] References Cited

U.S. PATENT DOCUMENTS

| | | | |
|---|---|---|---|
| 4,132,769 | 1/1979 | Osther | 424/1.1 |
| 4,520,113 | 5/1985 | Gallo et al. | 435/5 |
| 4,725,669 | 2/1988 | Essex et al. | 530/322 |
| 4,863,730 | 9/1989 | Karpas | 424/160.1 |

OTHER PUBLICATIONS

Prince et al. J. Cell. Biochem. Suppl. p. 44 1988. 12 Part B. J. of Cellular Biology.
Jackson et al. Lancet 2 647–651 1988.
Jon Cohen Science vol. 265:1028 1994.
Fahey et al. Clin Expt. Immunol. 88:1–5 1988.
Thouvenot et al., Appl. Environ. Microb. 45:16–23 (1983).
Essex, M. et al., Ann. Int. Med. 103:700–703 (1985).
di Merzo Veronese, F. et al., Science 231:1289–1291 (1986).
Robey et al. PNAS vol. 83:7023–7027 (1986).
Laskey et al. Science 233:209 (1986).
The Lancet, p. 566 (Mar. 7, 1987).
The Lancet p. 632 (Mar. 14, 1987).
Pan et al. J. Infec. Dis. 155:626–632 (1987).
Buchegger, F. et al., INCI 79:337–343 (1987).

*Primary Examiner*—Lila Feisee
*Attorney, Agent, or Firm*—Banner & Allegretti, Ltd.

[57] ABSTRACT

The disclosure relates to antibodies reactive with HIV-1 antigens and the use of such antibodies in vaccine preparations, immunotherapeutic preparations and assays for HIV-1.

1 Claim, 7 Drawing Sheets

ALKALINE PHOSPHATASE (U/L)

ANTI-HIV-1 NEUTRALIZING ANTIBODIES

RELATED APPLICATIONS

This application is a continuation-in-part application of Ser. No. 07/694,586, filed on May 2, 1991 now abandoned, which is a continuation-in-part application of Ser. No. 07/376,247, filed Jul. 6, 1989 now abandoned, which is a continuation-in-part of Ser. No. 07/215,867, filed Jul. 6, 1988, the contents of each of which are hereby incorporated by reference.

BACKGROUND OF THE INVENTION

Acquired immune deficiency syndrome (AIDS) is recognized as an epidemic in several areas of the world, including the United States. The Human Immunodeficiency Virus (HIV-1), a retrovirus, has been identified as the etiologic cause of the disease. HIV-1 was previously identified as Human T-Cell Lymphotropic Virus Type III (HTLV-III) and Lymphadenopathy Associated Virus (LAY). The groups at highest risk of infection with HIV-1 include homosexual and bisexual men and abusers of injected drugs. Other predictable high-risk groups are women artificially inseminated with sperm from infected donors and sexual partners of those in the AIDS risk groups. Recipients of blood transfusions, blood products or organs are also at risk of contracting AIDS. There is also evidence that HIV-1 is transmitted heterosexually as a result of sexual contact.

Known therapies are generally limited to regimens designed to treat the opportunistic infections and neoplasias associated with AIDS and its related illnesses. Very few treatments are available, however, which are directed towards the virus itself. Among the known antiviral drugs, which are believed to merely slow down viral replication and which do not cure the disease, much less prevent reinfection, are azidothymidine (AZT), alpha interferon, gamma interferon, azimexon and isopinosine. Remission of some Karposi sarcomas has been reported following treatment with alpha interferon, but the other antiviral drugs have not proven effective against HIV-1 infections. Immunomodulators, such as cimetidine and interleukin-2, which are intended to stimulate natural killer cell activity, have been reported as useful in the treatment of AIDS. Similar claims have also been made in connection with indomethacin, an antiinflammatory and prostaglandin inhibitor. In summary, current methods for treating individuals infected with HIV-1 are few, and largely ineffective.

Some therapeutic success has been observed following intravenous immunoglobulin treatment of HIV-infected children (Claveill et al., *Pediatr. Infec. Dis.* 5:S207 (1986)). It has been proposed that this treatment may be particularly beneficial to HIV-infected children. These children exhibit increased susceptibility to bacterial and viral infections due to both the destructive effects of HIV-1 infection and because infants possess an immature immune system. Specific anti-HIV-1 antibodies may have protective effects against infection. Passive administration of immunoglobulin from asymptomatic, HIV-1 positive individuals has led to a temporary clinical improvement in these individuals (Wendler et al., *AIDS Res. and Hum. Retroviruses* 3:177 (1987) and Rank et al., *Clin Exp. Immunol.* 69:231 (1987)). Another study has shown that children born to HIV-1 positive mothers were less likely to be infected with HIV-1 if they possessed serum with high neutralizing activity (Broliden et al., *AIDS* 3:577 (1989)). This indicates the presence of maternal antibodies which may confer protection when passed from mother to child. However, transfusion of serum from HIV-1 infected individuals is not feasible on a large scale, and administration of mouse monoclonal antibodies may be ineffective due to anti-murine immune responses in human patients.

While passive administration of protective immunoglobulin to HIV-1 infected patients is worthy of investigation, there are several obstacles to the production of such antibodies. Currently the only source of such antisera are from already infected individuals. Collection of their antisera presents risks to themselves and health care workers. In addition such immunoglobulin may contain virus particles which could be infectious to treated populations, thus complicating their production if not ultimately patient therapy.

SUMMARY OF THE INVENTION

The subject invention relates, in one aspect, to antibodies specifically reactive with an HIV-1 encoded product referred to herein as gp48. The gp48 reactive antibodies can be polyclonal or monoclonal, and preferably are of porcine origin.

The invention also relates to anti-HIV-1 antibodies which are produced by administering to a pig HIV-1 encoded protein in an amount sufficient to stimulate an immune response. The HIV-1 encoded protein can be purified from a lysate of HIV-1 infected cells or it can be produced by recombinant methods. The porcine antibodies produced in this manner can be formulated as a composition for administration as an immunotherapeutic to humans infected by the HIV-1 virus, or related viruses. The antibodies thus produced can also be used to isolate, by affinity purification methods, HIV-1 antigens. These antigens are enriched in immunodominant epitopes and are particularly useful for vaccine development.

Pigs produce antibodies which react with HIV-1 antigens which are not recognized by antibodies present in the serum of the vast majority of HIV-1 infected individuals. Components of this porcine serum exhibit an unprecedented HIV-1 virus neutralizing effect both in vitro and in vivo.

DETAILED DESCRIPTION OF THE INVENTION

Figure 1:
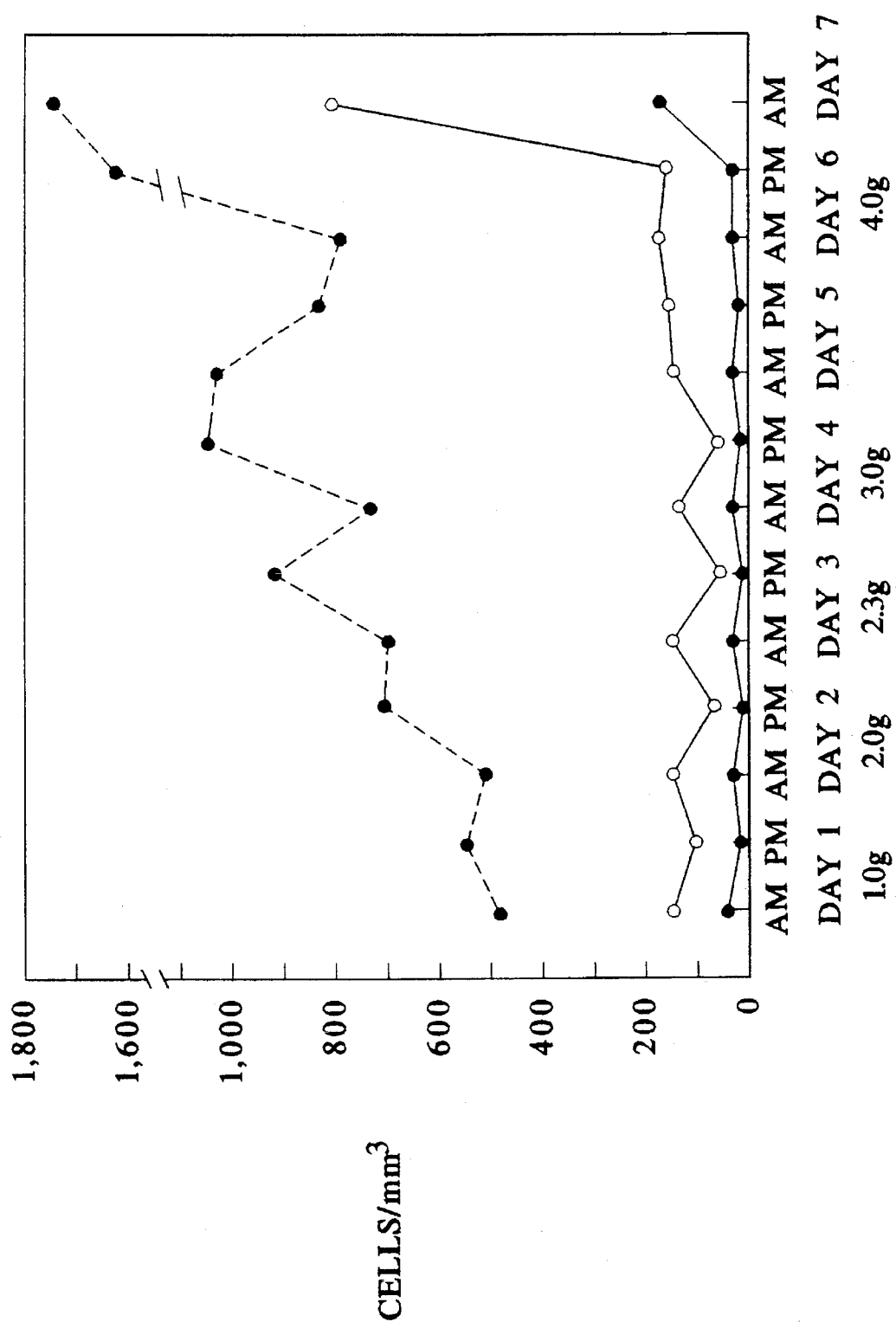
FIG. 1 is a diagram representing data from white blood cell counts and blood smears from an HIV-1 infected individual treated with a porcine anti-HIV-1 immunotherapeutic composition.

The present invention relates to polyclonal and monoclonal antibodies useful in both the prevention and therapeutic treatment of AIDS and related diseases, methods of producing such antibodies, and such treatments per se.

Viral Antigens

The genomic origins of many of the HIV-1 specific antigens have previously been established (Essex et al., *Ann. Int. Med.* 103:700 (1985); Pan et al., *J. Infect. Dis.* 155:626 (1987); Lelie et al., *Lancet* 1:632 (1987); Stute, *Lancet* 1:566 (1987); and Veronese et al., *Science* 231:1289 (1987)). The qaq gene encodes a protein having a molecular weight of 55,000 daltons (55 kDa) which can be cleaved into smaller proteins such as p24 (middle part of core) and p18, also named p17 (aminoterminus). The env gene encodes a 90 kDa protein richly glycosylated to yield a 160 kDa glycoprotein (gp160), which can be cleaved into a 120 kDa glycoprotein (gp120), the amino-terminus of the external vital membrane protein; and a 41 kDa glycoprotein (gp41), the carboxy-terminus transmembrane. Additionally, both the 64 kDa (p64) and the 53 kDa (p53) proteins have been shown to be related to the viral reverse transcriptase function. These proteins are encoded by the pol gene. Western blot systems are capable of detecting antibodies to all the protein bands described above except for the 90 kDa protein.

Klatzmann et al. first showed that HIV-1 selectively replicates in cells bearing the CD4 receptor, such as T4 lymphocytes (Klatzmann et al., *Nature*, 312:763 (1984)). Entry of the viral particles into the target cell is mediated by binding of the viral particle to the CD4 receptor of the target cell. Within the cell, the vital particle is uncoated and the vital RNA is reverse transcribed into DNA and incorporated into the genome of the infected cell. Thereafter, the cell initiates replication of HIV-1 virus.

The gp120 envelope glycoprotein plays a central role in the spread of HIV-1 infection, probably through cell-to-cell fusion. That is, budding virus on the cell surface binds to CD4 receptors on non-infected cells resulting in propagation of the virus. This phenomenon encompasses the so called syncytial reaction, resulting in the formation of giant cells (consisting of both infected CD4 bearing cells and noninfected CD4- cells). Certain populations of monocytes as well as a few other cell types express CD4 receptor and thus harbor the virus. The monocyte is thought to be able to carry the HIV-1 virus into the central nervous system. The CD4 bearing monocyte can thus harbor HIV-1 and be a dangerous carrier of the virus for a long period of time.

Preparation and Purification of Polyclonal Antisera

Anti-HIV-1 polyclonal serum is produced by immunizing an animal with HIV-1 viral lysate, purified or semi-purified components thereof. Alternatively, DNA isolated from HIV-1 virus can be used to produce HIV-1 antigen by recombinant methods. A variety of animals can be immunized with such a lysate including mice, rabbits, horses, cows, donkeys, sheep, goats, humans, monkeys, primates (including humans) and pigs. The preferred animals are humans, other primates and pigs with pigs being the most preferred animal for this purpose. The discussion which follows focuses on the pig.

Polyclonal anti-HIV-1 antibodies may be produced by immunizing a pig with purified, solubilized HIV-1 viral lysate, under conditions appropriate for the stimulation of an immune response in the pig. Injection schedules and composition formulations useful for immunization are well known to those skilled in the art. Preferably, the lysate used as immunogen stimulates the production of antibodies reactive with gp48 antigen in the Western blot assay described in the following section. It is the Western blot assay which is probably the most convenient method for determining whether the HIV-1 antigens present in a given viral lysate have stimulated the production of anti-HIV-1 antibodies.

Following administration according to standard protocol, the anti-HIV-1 antibodies can be harvested when the porcine antibodies reach a predetermined titer, for example, at least equal to that of a standard HIV-1 positive control serum. For example, when measured by use of an Electronucleonics Enzyme Linked Immunoabsorbent Assay (ELISA) test kit with a Behring ELISA Processor II (at 492 nm), such a positive control value is about 0.7. Preferably, employing that reference system, the porcine anti-HIV-1 is harvested at values in the range of about 0.7–2.2.

When a pig is immunized by a single vaccination with the HIV-1 preparation, and the antibodies are harvested by collecting blood from the pig within about 10 to 40 days (preferably 12 to 17 days) after vaccination, IgM isotype anti-HIV-1 is recovered. When, on the other hand, the pig is immunized by repeated vaccinations about every 14 to 120 days (preferably every 14 to 30 days), and the antibodies are harvested by collecting blood from the pig at least 20 days (preferably about 30 to 120 days) after the first such vaccination, IgG isotype anti-HIV-1 is recovered.

The immune porcine IgG may be purified by precipitation with polyethylene glycol (e.g., PEG 8000) prior to use. A suitable polyethylene glycol precipitation technique has been described by Carter and Boyd (*J.Immunol. Methods* 26:213 (1979)). This purification method eliminates any hemolysis from the blood and removes the majority of alpha and beta globulins. IgG products having concentrations of from about 4.5–5.5% w/v may thus be provided, analogous to human polyethylene glycol-precipitated immunoglobulin such as "Immunoglobulin 7S Human IV," marketed by Armour Pharma of Germany. This form of immunoglobulin may be intravenously administered (see, for example, Stanley, P. and Cole, P., *Lancet*, I:829 (1983)). A preferred purification method is by ion exchange chromatography or by immunopurification methods. Ion exchange chromatography is well known to those of skill in the art and exploits the charged nature of a molecule at a given pH to effect separation. Immunopurification methods involve the use of a moiety which specifically binds to the immunoglobulin in an immunoreactivity-based purification scheme. For example, it is known that protein A from *S. aureus* binds specifically to IgG. Protein G from streptococci, for example, is also useful for this purpose. Thus, a purification scheme can be designed wherein protein A is fixed to a solid support such as a column packing material. Porcine serum can be passed through the column and the IgG component is retained in the column and other serum components pass with the flow-through fraction.

Characterization of Porcine Anti-HIV-1 Sera by Western Blot Assay

Western blotting is a rapid sensitive assay for detecting and characterizing proteins by exploiting the specificity of an antibody for a particular antigen. The technique can use both monoclonal and polyclonal antibodies.

The HIV-1 Western blotting assay used within the present invention is a conventional assay (see e.g., Ausubel et al., *Current Protocols in Molecular Biology*, Greene Publishing Associates and Wiley-Interscience (1987). Solubilized HIV-1 (solubilized e.g., with sodium dodecyl sulfate, urea and/or other reducing agents) encoded proteins are separated by gel electrophoresis (e.g., SDS-PAGE) or other separatory techniques, (e.g., thin layer chromatography). The proteins are then electrophoretically transferred or blotted onto a solid substrate (e.g. nitrocellulose paper, nylon filters, etc.), where the proteins are bound irreversibly (referred to herein as an immunoblot). The paper is generally blocked (e.g., with a protein such bovine serum albumin) to prevent non-specific binding of antibody and is then incubated with the anti-HIV-1 specific antisera, or immunoglobulin purified from any such antisera or a monoclonal antibody having similar reactivity.

Non-specifically bound antibodies are removed by washing the immunoblot. Specifically bound antibodies are detected by contacting the immunoblot, treated as described above, with a labelled-anti-immunoglobulin (Ig) conjugate directed towards the anti-HIV-1 under conditions which allow the binding of the two antibodies to occur. The label on the second antibody can be a conventional label such as an enzyme (e.g., peroxidase), radioisotope or fluorescent molecule.

The HIV-1 encoded proteins which are separated on the basis of size and transferred electrophoretically to the solid substrate to form the immunoblot are prepared from an HIV-1 viral lysate. Lysate can be prepared, for example, by propagating the HIV-1 virus in T lymphocyte cultures (see e.g., Popovic et al., *Science* 224:497–500 (1984)). After mass propagation, the virus is purified and concentrated by sucrose density sedimentation and additional ultracentrifugation. The concentrated whole virus is then inactivated by disruption in detergent and high concentrations of salt. The material is verified for inactivation using tissue culture techniques and reverse transcriptase assays. It has been found that antigen fractions prepared in this manner contain the gp48 antigen.

It has been found that some commercial preparations of viral lysate contain the gp48 HIV-1 antigen region, the presence of which is preferred on the Western blot strips, whereas others do not. For example, a commercial source for viral lysate known to contain the gp48 antigen is Organon Teknika (Durham, N.C. 27704). The antigenic composition should be monitored with each new batch of viral lysate. The antigenic composition cannot be monitored by staining proteins separated by gel electrophoresis (for example with Coomasie blue) because viral proteins represent only about 10–15% of the proteins contained in a viral lysate prepared as described above. The majority of the proteins in such a preparation represent cellular proteins from the cells in which the virus was propagated.

To determine whether a particular viral lysate contains the gp48 epitopes, an immunoblot is prepared with the proteins of the viral lysate in question fixed to a solid substrate. The immunoblot is then contacted with sera from AIDS or ARC patients and positive control sera from HIV-1 immunized pigs. The typical results of such a Western blot using human serum as probe shows immunoreactivity of the following protein bands (although human sera can show a wide range of variability): p17/18, p24, p31, gp41, gp48, p53, p55, p64, gp120 and gp160. The porcine pattern, on the other hand, is highly reproducible. The predominant band is a broad glycoprotein band estimated to be at the 48,000 dalton to 53,000 dalton range. Other banding is observed reproducibly at p18, p24, p26, p31/33, p34, gp48, gp110, gp120 and gp160.

Polyclonal Anti-HIV-1 Activity

As demonstrated in the Exemplification, the polyclonal antisera of this invention is effective for human immunotherapy among other uses. It is not clear which of the antibody components present in the porcine polyclonal sera are responsible for the unexpected results reported herein. The results, however, clearly suggest the importance of antibodies reactive with the gp48 species. The gp48 antigen species appears to be envelope-derived as evidenced by the fact that it is heavily glycosylated.

The well known fact that most anti-HIV-1 antibodies are directed toward envelope components also suggests the importance of anti-gp48. The likely mechanism of the immunotherapeutic effectiveness of anti-gp48 is the induction of complement mediated lysis, and the recruitment of effector cells following recognition and binding by anti-gp48 of an HIV-1 envelope polypeptide which is displayed on the cell surface of an infected cell.

As discussed in the Exemplification, the anti-gp48 may also function in concert (either additively or synergistically) with other env and qaq antibodies such as anti-p24 core antibody and anti-p26. The importance of the anti-p24 antibody species is demonstrated dramatically in FIG. 5 which shows the rapid clearance of p24 core antigen from the serum following administration of the anti-HIV-1 antibodies of this invention to an infected human.

Immunotherapy

A major difficulty in AIDS therapy is the disappearance over time of "protective" immune responses during the evolution of the disease. Following a long latent period, the immune response to the virion is seen to decay, with emergence of the clinical manifestations of the disease. Passive immunotherapy may help to stave off these manifestations if such therapy is capable of decreasing the viral burden in infected individuals. For such therapy, high-titers of biologically active antibodies against HIV-1 are desirable. While such antibodies may be produced by screening human populations for individuals with high reactivity, large amounts of antisera would be difficult to obtain by this method.

As discussed above, the pig is an excellent source for biologically active human-like antibodies. Large quantities of highly biologically active antibodies can be produced by immunization with vital lysates as described here. As discussed in the Examples which follow, the resultant porcine antisera specifically recognizes HIV-1 antigens by multiple criteria. This includes assays that depend on recognition of denatured protein epitopes (immunoblotting) as well as those where the three-dimensional structure of the antigens is preserved (immunoprecipitation and flow cytometry). When compared, the porcine immune system responds similarly to the human immune system following natural infection, in terms of the proteins recognized.

In addition, the porcine antisera have biological properties important for anti-HIV-1 activity. This includes the ability to induce complement-mediated lysis, to neutralize HIV-1 infectivity in vitro, and to inhibit syncytia formation. While the first two properties are shared by many HIV-1 infected patients' antisera, inhibition of syncytia formation is seen only rarely in HIV-1 infected individuals. In related studies, more than 300 HIV-1 positive human serum samples have been screened for syncytia inhibition. Less than 7.5% exhibited syncytia inhibition, and this was typically of low titer. Sera with syncytia inhibitory properties typically possess high titers of inhibitory activity. As described in detail in the Examples, the porcine anti-HIV-1 has been compared with several human antisera with high syncytia inhibitory properties. This included H156, an antiserum with the highest level of syncytia inhibition detected. The porcine anti-HIV-1 surpassed even this antiserum for syncytia inhibitory activity. This documents the surprisingly high levels of biological activity present in the immune porcine antisera.

In addition to these considerations, porcine antisera developed by the methods outlined here represents clinically safe material. This is due to immunization protocols utilizing killed viral lysates, thereby obviating the danger of infectious transfer. In contrast, antibody preparations derived from infected individuals may possess infectious material. Taken together with the high degree of biological activity present in the specifically immune porcine antisera, and its low antigenicity in humans, such antisera is an excellent source of antibodies for passive immunotherapy for the treatment of AIDS.

As described in detail below, porcine anti-HIV-1 antibodies can be formulated as a composition for administration for human immunotherapy. Preferably, the antibodies are of the isotype IgG. The purification of the immunoglobulins from the serum of an immunized animal has been discussed above in the section of the Detailed Description entitled Preparation and Purification of Polyclonal Antisera. The preferred method for purification of HIV-1 specific antibodies is by immunological methods. While the description below is specifically directed toward intravenous administration, one skilled in the art will recognize that any mode of administration, by which sufficient quantities of the immunoglobulins are transferred in the circulatory system, can be used. Such other modes include, for example, subcutaneous, intramuscular, and intradermal. In general, the mode of injection is guided by practical considerations including, for example, the volume which is to be delivered, what buffers and other components are to be co-injected, and how quickly the immunogen should be released into the lymphatics or in the blood circulation.

The purified antibodies are suspended in a pharmaceutically acceptable carrier, preferably at a concentration of about 20% or less. The most preferred concentration is about 5%. Preferably, this solution has an ionic strength and pH sufficient to maintain the monomer content of the antibodies at a maximum level. The pH of the solution is preferably adjusted to about 3.5 to 5.0 by the addition of a physiologically acceptable acid (e.g. acetic acid).

Following the pH adjustment, the composition is treated to reduce its ionic strength also to maintain the monomer content of the antibodies at maximal levels. The preparation is then treated to render it tonic, i.e., to render it compatible with physiological conditions or render it physiologically acceptable upon injection. In this respect it is important to note that tonicity must be obtained without raising the ionic strength (as defined above) of the preparation. This end is achieved by adding to the preparation an amount of an amino acid, such as glycine or the like, or a carbohydrate, such as maltose, dextrose, fructose, or the like, or a sugar alcohol Such as mannitol, sorbitol, etc., or mixtures thereof sufficient to achieve tonicity. Thus, for example the preparation may be mixed with about 10% maltose (on a weight to volume basis) to render the preparation tonic.

After the above adjustment the product is sterilized, usually by sterile filtration through appropriate media, and then filled into final sterile containers. It is also possible to lyophilize the sterile product after filling into final containers. For intravenous use the lyophilized material is dissolved in physiologically-acceptable carrier prior to injection. If the product has not been made tonic prior to lyophilization, the lyophilized material must be dissolved in a diluent containing a physiologically-acceptable carrier and one of the aforementioned substances in an amount to render the preparation tonic.

For intravenous (I.V.) administration the recommended dosage range is about 10–20 grams (1 gram per 20 ml) for an adult administered I.V. over a period of 5 to 10 days. The first dosage (appr. 50 kg bodyweight) will be 1 gram (20 ml) composition on treatment day 1; 2 grams on treatment day 2; 2–3 grams on treatment day 3; 2–4 grams on treatment day 4; and 2–5 grams on treatment day 5, etc.

It is recommended to monitor the gp48 antibody concentration and, if possible, also p24 as well as p18 by the Western blot as described above beginning with testing prior to start of the first infusion of composition. The Western blot test should be performed preferably twice a day (morning and afternoon) in order to establish when free anti-gp48 (and, if possible, p24 and p18) begins to circulate in the patient's blood. The presence of free circulating gp48 antibody will give information about the "saturation" of binding sites with the composition indicating that the patient has received an optimal dosage of the antibodies. Furthermore, the HIV-1 p24 core antigen should be followed during the treatment to monitor clearance of p24 core antigen.

The initial rate of infusion of the composition is 0.01 ml per kg per minute for 30 minutes (if a dosage pump is used the does rate is often given in ml per hour). If no adverse reaction is observed the flow rate can then be increased to 0.03 ml to 0.04 ml per minute (not to exceed 0.04 ml per minute).

A preliminary PHASE 1 treatment protocol is described below:

| SUGGESTED DOSE SCHEDULE per kg body weight | | | | |
| --- | --- | --- | --- | --- |
| Day 1 | Day 2 | Day 3 | Day 4 | Day 5 |
| 20 mg/kg | 40 mg/kg | 40–60 mg/kg | 40–80 mg/kg | 40–100 mg/kg |

The patient's blood is tested 2 times a day using an HIV-1 Western blot. The next day's dose increase may be modified (smaller dose) if the Western blot shows a significant anti-gp48 reaction in the patient's blood. If no anti-gp48 band is found on the Western blot, dose increase should be according to the above schedule unless the patient's condition does not allow a higher dose. Furthermore, HIV-1 p24 core antigen should also be used to monitor the clearance of p24 antigen from the plasma phase.

The proposed dose escalation on consecutive days will depend largely on the appearance of free anti-gp48 evidenced by the Western blot test indicating saturation of gp48 binding sites in the patient and by an HIV-1 p24 antigen test. If side effects occur during a period of administration, the rate may be reduced, or the infusion interrupted until symptoms subside. The infusion may then be resumed at the rate which is comfortable for the patient.

The HIV-1 Western Blot is a convenient method for monitoring the course of treatment. As described in detail in the following Exemplification the accumulation of anti-p24 and anti-gp48 appears to be an important indicator. If these antibodies begin to accumulate it is an indicator that the concentration of their target molecules in the infected individual is decreasing. This phenomenon has been referred to herein as antibody saturation.

At the molecular level, it is presumed that anti-gp48 and related env antibodies are binding to an HIV-1 epitope or epitopes displayed on the surface of infected cells. This results ultimately in lysis of the infected cell which releases any mature virus which may be present in the cell. In addition p24 core (the immature, uncoated form of the virus) is also released. Clearly a decrease in the concentration of antibody target is due to a decrease in the vital load present in the individual.

Treatment is discontinued when the Western blot data shows gp48 and p24 saturation, and the blood work demonstrates the stimulation of new blood cell production by the bone marrow. It may be desirable to repeat the treatment periodically to be sure that the virus is cleared from the infected individual.

Preparation and Use of Monoclonal Anti-HIV-1

The monoclonal anti-HIV-1 antibodies of the present invention can be produced by antibody producing cell lines commonly referred to as hybridomas. The preferred monoclonal antibodies of this invention are reactive with the gp48 and p24 HIV-1 antigens.

The hybridomas are formed from the fusion of the antibody producing cell and an immortalizing cell line; that is, a cell line which imparts long term tissue culture stability on the hybrid cell. In the formation of the hybrid cell lines, the first fusion partner (the antibody producing cell) may be a spleen cell of an animal (preferably a pig) immunized against HIV-1 which produces anti-gp48 or anti-p24 core. The second fusion partner (the immortal cell) may be a lymphoblastoid cell or a plasmacytoma cell such as a myeloma cell, itself an antibody producing cell but also malignant. The preferred fusion partner is a porcine cell, or a cell from a human or other primate. Fusions can be accomplished using standard procedures (Kohler and Milstein, (1975) Nature 256,495-97; Kennett, R. (1980) in *Monoclonal Antibodies*, Kennett et al., Eds. pp 365–367, Plenum Press, N.Y.).

The hybridomas are screened for production of antibody reactive with HIV-1 antigens, and those which secrete reactive antibodies are cloned. The desired monoclonal antibodies can be recovered from the hybridoma supernatant using conventional techniques.

The monoclonal antibodies of the present invention can be used, for example, in the production of specific positive controls, as antibodies in ELISA antigen detection systems or, preferably, in the treatment of humans. As discussed above, the porcine antibodies directed toward the gp48 region and against gag components (e.g., p24 core) components appear to be of particular importance. Thus, monoclonals directed toward these components could be used, for example, in an immunotherapeutic regime in place of, or in addition to, the polyclonal anti-HIV-1 serum or components thereof.

Those skilled in the art will appreciate that naturally occurring HIV-1 antigens, fragments thereof, recombinant products or synthetic peptides can be used, for example, to stimulate antibody producing cells.

Vaccine Produced by Immunopurification

Porcine polyclonal antisera has been shown, as described herein, to be effective as a therapeutic agent when administered to an individual infected with the HIV-1 virus. Thus, the pig is recognizing immunodominant epitopes on the HIV-1 encoded viral proteins and producing antibodies which are capable of neutralizing the virus.

Such antibodies can be purified by conventional methods and exploited to isolate HIV-1 antigens to which they are reactive. By using this method one skilled in the art could produce an HIV-1 antigen preparation which is highly enriched for proteins which carry immunodominant epitopes. Such proteins are useful in vaccine compositions.

It is known that the immune system exhibits a preference for particular proteins (and as a consequence, particular epitopes) which depends upon the relative immunogenicity of the protein. Thus, by presenting only those proteins known to stimulate neutralizing antibodies, the immune system of an immunized person is encountering a collection of viral epitopes in ratios which are not encountered in a typical infection. Rather, the immune system is exposed to a composition rich in immunodominant epitopes.

Porcine anti-HIV-1 antibodies, purified as described above, are fixed to a solid substrate in a preferred embodiment. For example, the purified antibodies can be attached to a column packing material, such as CNBr activated Sepharose 4™ to produce an affinity column.

HIV-1 viral lysate (e.g. from Organon Teknika) in a solution having a pH of approximately 7.4, is then passed through the affinity column and HIV-1 antigens which are specifically reactive with the porcine antibodies are retained in the column whereas those which are not pass with the flow-through fraction.

The bound material is eluted from the affinity column by passing a pH gradient solution (approximately pH 7.4 to pH 3.0) through the column. At a pH of between about 5.0 to 3.0 the bound HIV-1 protein will elute. This material is concentrated and formulated into a composition which is administrable as a vaccine. Various vaccine formulations and administration schedules useful for human vaccination are well known to those skilled in the art.

Anti-Idiotypic Antibody Vaccine

Anti-idiotype gp48 antibodies (which are specific for the variable region of the immunoglobulin) suitable for the use in vaccines against the HIV-1 virus are a further feature of the present invention. The antiidiotype antibodies (Ab2) may be produced by:

a) immunizing an animal other than a pig against HIV-1 virus with a purified, stabilized preparation of HIV-1 which, when resolved in a Western blot assay, is characterized by binding in the gp48 region when reacted with anti-gp48 antibodies;

b) separating the antisera containing anti-gp48 from the blood;

c) immunizing a pig with the antisera containing anti-gp48 under conditions whereby anti-anti-gp48 are produced; and d) recovering the porcine anti-anti-gp48 for use as a vaccine.

The anti-antibodies produced in this manner are a template of gp48 to whose receptors the anti-gp48 antibody was directed.

Alternatively, the anti-anti gp48 idiotype antibodies may be purified, utilizing the pig as a cell factory to hybridize the immunized pig plasma cells with pig malignant plasma cells to give pig/pig hybridomas, or with hyman myeloma cells to give pig/human hybridomas. Such hybridomas produce antiidiotype monoclonal antibodies which can also be utilized in man as a vaccine.

In yet a further alternative, antiidiotype antibodies can be raised by first immunizing a pig with HIV-1 (gp48) and raising the antibodies in the pig. The antibodies can then be harvested, purified and prepared for immunization in another species host such as those noted hereinabove. This technique is preferred when producing antiidiotype antibodies as vaccines for animals.

From the preceding, it will be seen that HIV-1 virus or the corresponding synthetic peptide can be simulated as an antiidiotype antibody, with the thus-produced anti-anti AIDS proteins or constructed antigens being created from the templates of specific antibodies from another animal.

Assays for Detection of HIV-1 Infection Pre-Immune Response

One of the problems associated with the detection of HIV-1 infection is that they rely on the reactivity of HIV-1 antigen (typically fixed to an immunoblot) with antibodies present in the serum of infected individuals. However, a period of 3–6 months can elapse between infection and the appearance of anti-HIV-1 antibodies in the serum of the infected individual. Assuming a 15% increase in the number of infected individuals every 14 months, approximately 10% of the total infected population would, at a given point in time, test falsely negative for the disease. There would be no way to detect infection, for example, in blood donated by such individuals using currently available tests. However, by using the anti-gp48 antibodies of the present invention, detection of infection is possible in the patient serum prior to the appearance of detectable levels of anti-HIV-1 antibodies. As is described above, anti-gp48 lyses infected cells by binding to HIV-1 epitopes displayed on the surface of virus infected cells thereby inducing complement-mediated or effector cell induced lysis.

By contacting the anti-gp48 antibodies with lymphocytes from an infected individual for a short period of time followed by a secondary anti-porcine antibody labeled with a reporter group (e.g. fluorescein isothiocyanate), it is possible to detect infected cells months before any anti-HIV-1 antibodies are present in detectable levels in the serum of the patient.

EXAMPLES

Example 1
Preparation of Porcine Polyclonal Antisera and Immunoreactivity Assessment A pig of mixed Yorkshire breed (approximately 60 pounds in weight) was vaccinated once with purified HIV-1 lysate (ProtaTek, St. Paul, Minn.). The HIV-1 lysate was solubilized in Triton X100 in PBS buffer, pH 7.4. The concentration of the solubilized HIV-1 lysate was approximately 100 ug/ml. 1 ml of the HIV-1 lysate was mixed with 1 ml of Freund's complete adjuvant immediately prior to immunization of the pig. The vaccination was performed subcutaneously on 4 different locations on the pig's neck.

Blood was drawn from the pig's ear vein 15 days after the vaccination to test for the presence of IgM-specific HIV-1 antibodies. Serum was separated by centrifugation and tested for the presence of IgM using an ElectroNucleonics HIV-1 ELISA Test Kit. The antibody titer was measured. Goat antihuman IgM horseradish peroxidase (Calbiochem, LaJolla, Calif.) at a dilution of 1:2000 was used to detect IgM binding. The serum was also tested on HIV-1 Ab Western blot nitrocellulose strips using the method described herein.

Porcine serum drawn from the pig prior to the vaccination was tested for a baseline value. The pig serum tested positive for IgM anti-HIV-1 by ELISA (0.626) with the cut-off (that value regarded as positive for HIV-1) at 0.189. The IgG anti-HIV-1 was found to be 0.031 (far below the cut-off).

In an HIV-1 Ab Western blot assay performed as described in the Detailed Description section above, the IgM anti-HIV-1 serum bound to gp48 which was detected as a diffuse broad band ranging from a molecular weight estimated to be at 48,000 daltons to about 53,000 daltons. Weak gp160, and p24 bands were also observed. No gp41 band was detected.

The pig was revaccinated with the same batch of solubilized HIV-1 without Freund's adjuvant (100 ug HIV-1/ml 0.1%–1% Triton X100 in PBS, pH 7.4) every 14 days (5 times). Blood was drawn from the ear vein just prior to each vaccination and tested for the presence of IgM and IgG HIV-1 antibodies in HIV-1 ELISA and on the HIV-1 Ab Western blot assay. The IgG titers exceeded the IgM titers commencing 28 days after the initial vaccination. Upon resolution by the Western blot assay, the IgG serum sample exhibited a gp48 band but no gp41 band.

Example 2
Anti-HIV-1 Reactivity with Recombinant Envelope Protein

In another set of experiments, Yorkshire mixed breed pigs were immunized with HIV-1 lysate which had been enriched in envelope glycoprotein (Organon Teknika). Antisera were obtained following the third boost. Antisera were characterized by ELISA and Western blotting prior to further analysis. Immunoreactivity was further assessed by immunoprecipitation, radioimmunoassay and flow cytometry.

Immunoprecipitation studies were conducted by labeling protein expressed in Chinese hamster ovary (CHO) cells containing a recombinant DNA construct (designated HXB2) which encodes gp160 envelope protein. The HXB2 envelope construct was described by Sodroski et al. (Nature 322:470 (1986)) and was obtained from the NIH AIDS repository. The cell labeling and lysis was conducted as described by Weiner et al. (Proc. Natl. Acad. Sci. USA 85:6077 (1988)). Briefly, $^{35}S$ labeled cells were extensively washed with TBS prior to lysis in PI/RIPA buffer [1% NP40, 0.1% Deoxycholate, 0.15M NaCl, 0.01M sodium phosphate, pH 7.4, 1 mM PMSF, 2 mM EDTA, 10 mM sodium fluoride, 10 mM sodium pyrophosphate, 400 uM sodium orthovanadate, 10 mM iodacotamide (to prevent acetylation) and 1 mM ATP]. Lysates were precleared with irrelevant serum coupled to agarose beads for 30 minutes. Pre-cleared supernatants were subjected to immunoprecipitation with various antibodies and protein A-agarose beads, or with antibodies directly conjugated to agarose beads (e.g. Sepharose CL48™). The immunoprecipitated material was eluted from the antibody-bead complex with 25 ul of SDS sample elution buffer (2% SDS, 20% glycerol, 50 mM Tris-HCl, pH 6.8, containing 5% 2-mercaptoethanol) and boiled for 3 minutes. Molecular weight standards (Pharmacia), visualized with Coomassie Blue dye were included in all slab gels. Samples were resolved by 6% SDS-polyacrylamide gel electrophoresis. The dried gels were exposed to x-ray film at −80° C.

The antibodies used for immunoprecipitation included 1) non-immune porcine serum; 2) anti-HIV-1 porcine serum; 3) control immunized rabbit serum; human HIV-1 positive serum (patient 3); normal human serum; and human HIV-1 positive serum (patient 2). The porcine anti-HIV-1 serum specifically immunoprecipitated recombinant gp160 at levels higher than that seen with HIV-1 positive human serum. Non-immune porcine serum had little ability to precipitate gp160. This confirms the ability of porcine anti-HIV-1 to bind to conformational epitopes of gp160.

A sandwich radioimmunoassay was conducted by attaching recombinant HIV-1 antigen to the wells of multi-welled plates. The antigens attached were gp120 or gp160 (Micro-Gene Sys, Inc., Meridan, Conn. 06450). The recombinant protein was suspended in 0.05M carbonate/bicarbonate buffer pH 9.6 (CBC) at a concentration of 1 ug/ml. 50 ul (i.e. 50 ng) was immobilized in wells overnight at 4° C. Plates were washed with PBS and non-specific sites were blocked with 1% BSA in PBS overnight at 4° C. Dilutions (1:30 and 1:300) of porcine anti-HIV-1 or porcine anti-HIV-2 were made and 100 ul were incubated in the gp120 and gp160 coated wells for 2 hours at room temperature (RT). Plates were washed with PBS and incubated with 75,000 cpm of $I^{125}$ labelled protein A for 2 hours at RT. Plates were then washed extensively, dried, cut and counted in a gamma counter.

Results showed specific binding of porcine anti-HIV-1 to recombinant gp120 and gp160. No significant binding was observed with porcine anti-HIV-2 or with porcine non-immune serum. The levels of reactivity were similar to those observed using human AIDS or ARC patients as antibody source.

Flow cytometry studies were conducted using CHO cells expressing the HXB2 envelope construct described above in connection with the immunoprecipitation studies. Cells were removed from tissue culture and washed twice in FACS medium (Hanks' balanced salt solution (Gibco) supplemented with 2% fetal calf serum, 0.2% sodium azide, and 10 mM Hepes). $1\times10^6$ cells were incubated in 0.1 ml of FACS medium with 2 ul of porcine anti-HIV-1 or control antisera (pre-immune antisera) for 1 hour at 4° C. Cells were diluted in 2.5 ml of FACS medium, pelleted by centrifugation at 1000×g and washed twice more with 2.5 ml of FACS medium per wash. Following the final wash, the cell pellet was gently resuspended and cells were incubated with 0.1 ml of FITC-conjugated rabbit anti-porcine IgG (reactive with antibody heavy and light chains, Miles Laboratories) diluted 1:20–1:50 in FACS medium for 1 hr. at 4° C. Cells were diluted and washed as after the first incubation. The cell pellet was finally resuspended and the cells were fixed in 0.5–1.0 ml 2% paraformaldehyde-PBS. Samples were run on Becton Dickinson FACS IV (routinely 20,000 cells per sample). Specific fluorescence was quantitated by subtracting the median fluorescence channel of cells stained with FITC-conjugated secondary antisera alone (negative control) from the median fluorescence channel of cells stained with specific antibody followed by FITC-conjugated anti-porcine immunoglobulin (positive staining).

Staining on FACS by the porcine antisera was compared with staining by normal porcine serum. As is demonstrated, the porcine anti-HIV-1 produced staining of envelope expressing cells, while envelope expressing cells stained with normal porcine serum were negative. Staining on FACS was also investigated for H9/IIIb cells chronically infected with HIV-1 (cell line obtained from Dr. Hoxie, University of Pennsylvania). As a positive control, staining of uninfected H9 cells with anti-CD4 antibody Leu3a was performed. The porcine anti-HIV-1 produced higher levels of staining on HIV-1 infected H9 cells than AIDS patients' serum. These results confirm the ability of the porcine antisera to bind conformational epitopes present on the HIV-1 envelope.

In preliminary experiments, the recombinant gp 160 and gp 120 proteins were used to immunize pigs. The antibodies produced by these pigs demonstrated reactivity in the 41–43 kd range in a Western blot which may correlate with the position of the non-glycosylated form of the gp 48 antigen.

Two 3 to 4 months old Yorkshire mixed breed pigs were immunized with HIV-1 recombinant envelope proteins. One pig was immunized with recombinant gp160. The vaccine was made by mixing 2.5 micrograms of recombinant gp160 protein in 1% sodium dodecyl sulphate (SDS) with Freud's Complete Adjuvant. The pig was then vaccinated subcutaneously in the neck region. Twenty hours after this first immunization, another 2.5 micrograms of recombinant gp160 in 1% SDS was mixed with Freund's Incomplete Adjuvant. Immediately following preparation of the mixture the pig was boostered with this vaccine. The same composition was used as a booster 12 days after the first vaccination. The vaccine for the 4th vaccination was made by boiling 2.5 microgram of gp160 in 1% SDS at 65° to 70° C. for 40 minutes. The boiled preparation was then mixed with Freund's Incomplete Adjuvant and immediately injected subcutaneously into the neck region of the pig.

Blood was drawn from the ear vein at day 1 (baseline draw prior to 1. vaccination), at day 12 and at day 50. The serum specimens were tested in HIV-1 Western Blot. The baseline specimen showed no visible protein bands. The day 12 specimen showed a weak 160, a weak 120 and weak band in the 41–43 kd region. The day 50 specimen showed a strong gp160, a weak gp120, a distinct 110 kd band, a gp48 broad band and a gp41 band.

Another pig was immunized with recombinant gp120. The vaccine consisted of 2.5 micrograms of recombinant gp120 in 1% sodium dodecyl sulphate mixed with FCA for the first vaccination. The second vaccination was done by mixing 2.5 micrograms of recombinant gp120 in 1% SDS with FIA, and the booster vaccination was performed approximately 20 hours after the first vaccination. The vaccine used for the third vaccination was prepared exactly as the second vaccine. The fourth vaccination was done using 2.5 micrograms of recombinant gp120 in 1% SDS, boiled at 65° to 70° C. for a period of 40 minutes and then mixed with FIA immediately prior to the vaccination. The vaccinations were performed in the same sequence and with the same intervals as the vaccination of the pig (vaccinated with recombinant gp160) described above.

Blood was drawn from the ear vein at day 1 (baseline draw prior to 1. vaccination), at day 12 and at day 50. The serum specimens were tested by HIV-1 Western Blot. The baseline specimen showed no visible protein bands. The day 12 specimen showed a weak gp160, a weak g120 and a weak band in the 41–43 kd region. The day 50 specimen showed a strong gp160, a strong gp120, a distinct 110 kd band, a gp48 broad band and a weak gp41 band (weaker than the gp48 and gp41 bands found in serum from the pig immunized with recombinant gp160).

Example 3

Cytoxic Effect of Porcine Anti-HIV-1 on Infected Cells in Culture

The porcine anti-HIV-1 was tested for cytotoxic effect on infected cells in culture. The following cell lines were employed: HTVE (a T lymphoma immortalized by oncogenes); CEM (a T lymphoma immortalized by oncogenes); MT-2 (a T lymphoma infected with HTLV-1); PI-M38 (a mouse macrophage); and Daudi (a B cell line derived from a patient with Burkitt's lymphoma). The infectivity of these cells, when challenged with a sufficient quantity of HIV-1 virus, is shown in Table I.

TABLE I

| | Characteristics of Cell Lines Tested | |
|---|---|---|
| Cell Line | HIV-1 Infectivity | CD4 |
| HTVE | +++ | + |
| CEM | +++ | + |
| MT-2 | +++ | + |
| PI-M38 | − | − |
| Daudi | − | − |

The cells bearing CD4 receptors were readily infected by HIV-1 (about 90% of the HTVE, CEM and MT-2 cells were infected). The cell lines were infected with HIV-1 (2.5 KS 050988) at an activity of 106 infective units per ml and then treated with porcine anti-HIV-1 immune sera (prepared as described above) and control sera as follows:

1. Various test cells were incubated with HIV-1 at 37° C. for 2 hours in 24 well plates, and then immune porcine sera and control sera were added thereto;

2. Immune porcine sera and control sera were added to the cells in 24 well plates, incubated for 2 hours, and then the HIV-1 was added thereto; and 3. Immune porcine sera and control sera plus the HIV-1 were added directly to the cells in 24 well plates, in a dilution of 1:50.

All sera used for incubation were diluted in RPMI 1640 and 10% fetal bovine serum FBS at the following dilutions: 1:1, 1:8, 1:32, 1:128, 1:512. The plates were read after every 24 hour period under phase microscopy. General cell morphology of the cells were noted, especially viability, giant cell, syncytia formation, cytopathic effect (CPE) and lysis.

Surprisingly, as shown in Table 2, approximately 90% of the HTVE, CEM and MT-2 (susceptible to HIV-1 transfection) cells were lysed at a serum dilution of up to 1:128 of the heat treated (56° C., 30 minutes) immune porcine sera and control sera (but not by the porcine negative control serum). The PI-M38 mouse macrophages and Daudi cells were not lysed and were not susceptible to infection with the HIV-1 virus. It should be noted that the amount of virus added ($10^6$ infective units/ml) to the various cells was probably 100 to 1000 times higher then what would be detected in HIV-1 infected patients when they have viremia outbursts.

TABLE 2

Lysis of Different Cell Lines by Porcine Anti-HIV-1

| Cell Line | HIV-1 Infectivity | % Lysis by Pig IgM Anti-HIV-1 | By Pig IgG Anti-HIV-1 | By Pig Non-Immune IgG 1:2 |
|---|---|---|---|---|
| HTVE | +++ | 90% | 90% | 1% |
| CEM | +++ | 90% | 90% | 1% |
| MT-2 | +++ | 90% | 90% | 1% |
| PI-M38 | 0 | 1% | 1% | 1% |
| Daudi | 0 | 1% | 1% | 1% |

As a control for the cytopathic effect, the same cell lines were not infected with HIV-1 prior to the incubation with porcine HIV-1 immune or non-immune serum. None of the uninfected cells showed any significant cytopathic effect after 24 hours. From this experiment it was concluded that the porcine anti-HIV-1 has a specific cytopathic effect on HIV-1 infected cells.

Based upon the cytotoxic effect of porcine immuneserum on HIV-1 infected cells described above (Table 2), the following experiment was done in order to establish whether different complement inactivated sera would reveal any ADCC effect on infected as well as non-infected cell lines. The experiment included evaluation of the cytotoxic effect on the same cell lines described above by various types of heat inactivated sera including:

1) porcine anti-HIV-1 IgM serum;

2) porcine anti-HIV-1 IgG serum;

3) human anti-HIV-1 serum;

4) porcine non-immune serum; and 5) human non-immune serum.

All sera were sterile filtered through a 0.45 um filter and subsequently heat inactivated at 56° C. for 30 minutes in order to inactivate complement activity. The above described sera along with $10^6$ infective units of HIV-1/ml were added directly to cultures of the 5 cell types described above in 24 well plates. The cells were then incubated at 37° C. for 24 hours and then examined by invert cell microscopy for detection of cytopathic effect (see Table 3, 4, 5, 6, and 7). The sera were diluted in RPMI 1640 at the following dilutions prior to adding HIV-1: 1:1, 1:8, 1:32, 1:128 and 1:512.

TABLE 3

Cytotoxic Effect on Cells by Sera Tested Porcine HIV-1 IgM serum

| Cell Type | Serum Dilutions | | | | |
|---|---|---|---|---|---|
| | 1:1 | 1:8 | 1:32 | 1:128 | 1:512 |
| HTVE | ++++* | +++ | +++ | +++ | + |
| CEM | ++++* | +++ | +++ | +++ | + |
| MT-2 | ++++* | +++ | +++ | +++ | + |

TABLE 3-continued

Cytotoxic Effect on Cells by Sera Tested Porcine HIV-1 IgM serum

| Cell Type | Serum Dilutions | | | | |
|---|---|---|---|---|---|
| | 1:1 | 1:8 | 1:32 | 1:128 | 1:512 |
| Daudi | ++++* | – | – | – | – |
| PI-M38 | ++++* | – | – | – | – |

*cell cytotoxicity observed after 12 hours, probably due to the high serum concentration (nonspecific cytotoxicity).
+++: 75% CPE; ++: 50–75% CPE; +: 20–50% CPE; (+): 20% CPE; –: 1% CPE.

TABLE 4

Cytotoxic Effect on Cells by Sera Tested Porcine HIV-1 IgG serum

| Cell Type | Serum Dilutions | | | | |
|---|---|---|---|---|---|
| | 1:1 | 1:8 | 1:32 | 1:128 | 1:512 |
| HTVE | ++++* | +++ | +++ | +++ | ++ |
| CEM | ++++* | +++ | +++ | +++ | + |
| MT-2 | ++++* | +++ | +++ | +++ | + |
| Daudi | ++++* | – | – | – | – |
| PI-M38 | ++++* | – | – | – | – |

*cell cytotoxicity observed after 12 hours, probably due to the high serum concentration (nonspecific cytotoxicity).
+++: 75% CPE; ++: 50–75% CPE; +: 20–50% CPE; (+): 20% CPE; –: 1% CPE.

TABLE 5

Cytotoxic Effect on Cells by Sera Tested Human anti HIV-1 Serum

| Cell Type | Serum Dilutions | | | | |
|---|---|---|---|---|---|
| | 1:1 | 1:8 | 1:32 | 1:128 | 1:512 |
| HTVE | ++++* | ++++* | (+) | (+) | (+) |
| CEM | ++++* | ++++* | (+) | (+) | (+) |
| MT-2 | ++++* | ++++* | (+) | (+) | (+) |
| Daudi | ++++* | ++++* | – | – | – |
| PI-M38 | ++++* | ++++* | – | – | – |

*cell cytotoxicity observed after 12 hours, probably due to the high serum concentration (nonspecific cytotoxicity).
+++: 75% CPE; ++: 50–75% CPE; +: 20–50% CPE; (+): 20% CPE; –: 1% CPE.

TABLE 6

Cytotoxic Effect on Cells by Sera Tested Porcine non-immune serum

| Cell Type | Serum Dilutions | | | | |
|---|---|---|---|---|---|
| | 1:1 | 1:8 | 1:32 | 1:128 | 1:512 |
| HTVE | ++++* | ++++* | (+) | (+) | (+) |
| CEM | ++++* | ++++* | (+) | (+) | (+) |
| MT-2 | ++++* | ++++* | (+) | (+) | (+) |
| Daudi | ++++* | ++++* | – | – | – |
| PI-M38 | ++++* | ++++* | – | – | – |

*cell cytotoxicity observed after 12 hours, probably due to the high serum concentration (nonspecific cytotoxicity).
+++: 75% CPE; ++: 50–75% CPE; +: 20–50% CPE; (+): 20% CPE; –: 1% CPE.

TABLE 7

Cytotoxic Effect on Cells by Sera Tested
Human non-immune serum

| Cell Type | Serum Dilutions | | | | |
|---|---|---|---|---|---|
| | 1:1 | 1:8 | 1:32 | 1:128 | 1:512 |
| HTVE | ++++* | ++++* | (+) | (+) | (+) |
| CEM | ++++* | ++++* | (+) | (+) | (+) |
| MT-2 | ++++* | ++++* | (+) | (+) | (+) |
| Daudi | ++++* | ++++* | – | – | – |
| PI-M38 | ++++* | ++++* | – | – | – |

*cell cytotoxicity observed after 12 hours, probably due to the high serum concentration (nonspecific cytotoxicity).
+++: 75% CPE; ++: 50–75% CPE; +: 20–50% CPE; (+): 20% CPE; –: 1% CPE.

AS seen in tables 3 to 7, all sera tested showed nonspecific cytotoxicity as would be expected in dilutions 1:1 and 1:8. HIV-1 infected cells incubated with porcine HIV-1 IgM serum showed loss of viability within 24 hours. No change in viability and no CPE was found in Daudi and PI-M38 cells in any dilutions except at 1:1 and 1:8. At dilution of 1:512 the loss of viability declined and after 72 hours of observation and lysis percentage of 75% or more was observed in MT-2, CEM and HTVE at a serum dilution of 1:512. No significant CPE effect was observed in Daudi and in PI-M38 cells.

When the HIV-1 infected cells were incubated with porcine HIV-1 IgG serum dilutions ranging from 1:32 to 1:128, they showed significant CPE 24 hours after addition of the immuneserum. No change in viability and no CPE was found in Daudi and PI-M38 cells. At a dilution of 1:512 the CPE effect within 24 hours after exposure to the immuneserum declined significantly, and after 72 hours post infection 3+CPE/lysis was observed in HTVE, CEM, and MT-2.

Human anti-HIV-1 serum (Western Blot positive showing gp160/120, gp41, p55, and p24) was toxic to all cells at concentrations ranging from 1:1 to 1:8. No significant interference with the HIV-1 infected cells was observed at 24 hours post exposure. However, at 72 hours post exposure the cell cultures showed 3+CPE/lysis. When considering the heat inactivation of the sera prior to application to the cell cultures, the classical complement pathway would be inactivated. The lack of 24 hour CPE effect using inactivated human anti-HIV-1 serum may be due to the lack of complement source. Porcine and human non-immune serum (i.e., HIV-1 antibody negative sera) likewise showed no significant CPE effect after 24 hours and CPE/lysis after 72 hours, resembling the results obtained using human anti-HIV-1 serum. There is a significant difference in the 24 hour CPE effect in cells incubated with the HIV-1 immuneserum independently whether it was harvested as anti-HIV-1 IgM specific antiserum or as HIV-1 IgG specific antiserum.

Example 4

Rabbit Complement Mediated Lysis and Antisyncytial Activity of Porcine Anti-HIV-1

An important mechanism of immune protection against infection is antibody dependent cytotoxicity. This is in part due to the ability of specific antibodies to bind infected cells and induce complement mediated lysis of these cells. The porcine anti-HIV-1 were therefore tested for the ability to induce lysis of HIV-1 envelope expressing cells. HIV-1 infected H9 cells were incubated in 96 well plates with a 1:10 dilution of heat inactivated porcine or human immune antisera or control sera (20 min, 4° C.) followed by the addition of rabbit complement according to standard protocols (see e.g., Williams et al., Cell. Immunol. 10:35–45 (1987)). Lysis was determined by visual inspection and graded as 0–4+based on quantitation of the intact cells remaining in the well.

TABLE 8

Lysis of HIV-1 Infected Cells by Various Antisera

| Sample | Complement Mediated Lysis |
|---|---|
| Normal Human Serum | 0 |
| H156 | ++++ |
| Normal Porcine Serum | 0 |
| Porcine anti-HIV-1 | ++++ |

The results are depicted in Table 8. Porcine anti-HIV-1 elicited complement mediated lysis of HIV-1 envelope expressing cells, but not of mock transfected controls. Complete lysis of these cells was evident at several dilutions of antisera, comparable to that seen with HIV-1 positive patient sera. This implies that the porcine anti-HIV-1 displays similar complement fixing activity as HIV-1 positive sera. H156 represents serum from an HIV-1 asymptomatic individual with unusually high neutralizing and anti-syncytial activity.

The porcine anti-HIV-1 was capable of neutralizing HIV-1 infectivity in the absence of complement. For this determination, infectious transfer was determined as follows. HIV-1 containing supernatants from chronically infected H9 cells were preincubated with dilutions of antisera, placed on CEM target cells, and incubated for 24 hours prior to being washed, and reset-up in fresh growth media. Cells were assayed 10 days later for reverse transcriptase activity by the following protocol. Cells to be assayed were pelleted by centrifugation and 50 ul of culture supernatant was collected from each well for assay. 25 ul of supernatant was plated in 96 well round bottomed plates and 50 ul of transcriptase cocktail was added to each well. Cocktail was 50 mM Tris-HCl pH 8.0, 20 mM DTT, 0.6 mM $MnCl_2$, 60 mM NaCl, 0.05% NP-40, 5 ug/ml dT (oligodeoxythymidilic acid), 10 ug/ml poly A (polyriboadenylic acid), 10 uM dTTP, 1 Ci/mM $^{32}P$ dTTP. Plates were then incubated for 60 minutes at 37° C. After incubation, samples were spotted onto Whatman DEAE-81 paper, washed extensively and dried. Membranes were then analyzed by autoradiography with XAR film at −70° C. for 6 hours. Neutralization titers represent the highest dilution of antisera tested which completely inhibited reverse transcriptase activity.

TABLE 9

Neutralization of HIV-1 Infectivity by Various Antisera

| Sample | Neutralization Titer |
|---|---|
| Normal Human Serum | 0 |
| Pooled AIDS Patients' Sera | 1:4 |
| Patient 15 | 1:16 |
| Normal Porcine Serum | 0 |
| Porcine anti-HIV-1 | 1:64 |

As shown in Table 9, the porcine anti-HIV-1 demonstrated extremely high titers of neutralizing activity against the HXB2 isolate of H9/IIIB. These titers were higher than seen in most AIDS and ARC patients' sera. This indicates high neutralizing activity for the porcine anti-HIV-1.

The porcine antisera also was quite potent in inhibiting HIV-1 induced syncytia formation. Syncytia form as a result of the action of the HIV-1 envelope induced cell-cell fusion, and is thought to represent the early events in viral entry. Syncytia inhibition is rarely found in antisera from patients with AIDS or ARC, and when found is usually present in low titer. Prior studies indicated that the frequency of syncytia inhibiting activity in over 300 HIV-1 positive patients' sera assayed (including AIDS, ARC, and HIV positive asymptomatic) is less then 8%. Of these, titers of more than 1:8 were found in fewer than 2% of the sera tested. The porcine anti-HIV-1 was assayed for syncytia inhibition, and the results were compared with the most potent syncytia inhibiting HIV-1 positive patients' sera previously demonstrated.

TABLE 10

HIV-1 Induced Syncytia Formation

| Samples Tested* | Dilution | | | | |
|---|---|---|---|---|---|
| | 1/4 | 1/8 | 1/16 | 1/32 | 1/64 |
| Neg Control | 4L | 4L | 4L | 4L | 4L |
| NHS | 4L | 4L | 4L | 4L | 4L |
| PS3 | 1M | 4L | 4L | 4L | 4L |
| PS4 | 3M | 4L | 4L | 4L | 4L |
| LEU 3A | 0 | 0 | 0 | 0 | 0 |
| P-Anti-HIV | 0 | 0 | 0 | 0 | 2S |
| PS-A10 | 0 | 0 | 2M | 4M | 4M |
| H156 | 0 | 0 | 0 | 1 | 3M |

Supt T1 cells were used as target cells in the syncytia formation assay. They fuse rapidly when cocultured with HIV-1 (H9/IIIb) producing cell lines. HIV infected cells were plated in 96 well plates (104 cells/well in RPMI 1640+10% FCS) and incubated with or without dilution of antisera for 30 minutes at 37° C. Target cells were then added ($5 \times 10^5$/well) and the number of syncytia were qualitatively determined after the incubation periods. In Table 10, syncytia are scored numerically from 0 to 4, with 4 being multiple syncytia widely distributed and 0 indicating no syncytia observed. The size of the syncytia is recorded as S (small), M (medium) and L (large syncytia). Samples tested are: NHS (normal human serum); PS3 (Patient Serum 3); PS4 (Patient Serum 4); Leu 3A (monoclonal antibody Leu 3A anti-CD4 reagent which directly interferes with gp120-CD4 interactions); P-Anti-HIV (Pig anti-HIV antiserum); PS-A10 (Patient Serum A10 which inhibits syncytia); H156 (Patient serum H156 with high antisyncytia activity).

The results are demonstrated in Table 10. Porcine anti-HIV-1 completely inhibited syncytia at dilutions as low as 1/32, and still retained activity at dilutions of 1/64. In contrast, most HIV-1 positive patients' sera were ineffective at any dilution, and even the most potent syncytia inhibiting patients' antisera began to lose effectiveness at 1/16–1/32 dilutions. This potent syncytia inhibition is reminiscent to the effectiveness of the Leu3a monoclonal antibody, which completely abrogates binding of HIV-1 to CD4 molecules.

Example 5

Effect of Porcine Anti-HIV-1 on Whole Blood of a Healthy Subject 60 ml of whole blood was drawn from a 36 year old healthy female (HIV-1 Ab negative and HIV-1 Quick Western Blot negative). The blood was drawn in tubes containing ACD anticoagulant. 5 ml of whole blood was drawn in a tube for white cell count. To separate aliquots of the freshly drawn blood were added: a) porcine anti-gp 48 IgM type serum; b) porcine anti-gp 48 type IgG serum; c) partially purified anti-gp type IgG; and d) an untreated control.

The partially purified IgG-type anti-HIV-1 was purified using a method described by Carter, R. J. and N. D. Boyd (*J. Immunol. Methods* 26:213 (1976)). The psoralen/UV treated sera and partially purified anti-HIV-1 IgG were added to the whole blood at a dilution of 1:50. The IgG concentration prior to dilution in the partially purified product was measured as 1,021 mg/100 ml. In the anti-HIV-1 serum, the IgG concentration was measured as 1,103 mg/100 ml using Behring Diagnostics NOR-partigen plates.

Each blood sample was incubated for 2 hours at room temperature on a tube rocker followed by incubation at 37° C. for 20 hours. The lymphocytes were isolated from the whole blood by an independent laboratory using Hypaque-Ficoll gradient centrifugation. The lymphocytes were then reacted with OKT4 monoclonal antibody and OKT8 monoclonal antibody, and blind-coded for cytophometric measurement. The lymphocyte populations were measured on an Ortho Flow cytophotometer having an approximately 12 micron gate. The results are shown in Table 3.

Table 11 shows there were no significant changes in the percentages of OKT4 and OKT8 cells in the anti-HIV-1 treated whole blood, as compared with the untreated whole blood. Accordingly, it appears that anti-HIV-1 does not alter the proportion of T4 and T8 cells in a healthy subject.

TABLE 11

Effect of Treatment of T4 and T8 Cell Populations of Healthy Subject with Anti-HIV-1

| Lymphocyte Marker | Percentage of Cells | Absolute Numbers/sq mm |
|---|---|---|
| A. Whole Blood Treated with Anti-HIV-1, IgM | | |
| OKT4 | 58 | 2544 |
| OKTS | 35 | 1535 |
| B. Whole Blood Treated with Anti-gp 48, IgG | | |
| OKT4 | 55 | 2413 |
| OKT8 | 18 | 1228 |
| C. Whole Blood Treated with Anti-gp 48, Semipure IgG | | |
| 56% | 56 | 2457 |
| 31% | 31 | 1360 |
| D. Untreated Whole Blood | | |
| OKT4 | 53 | 2325 |
| OKT8 | 33 | 1448 |

Example 6

Anti-HIV-1 Treatment of AIDS Whole Blood

A 35-year old homosexual male without AIDS or ARC who was previously found to be HIV-1 ELISA positive and confirmed HIV-1 Western blot positive (p18, p24, p31/33, gp41, p53, p55, p64, gp120, gp160), and was rechecked and found to have the same HIV-1 antibodies about a year later was used for this experiment. 60 ml of blood were drawn for the lymphocyte experiment and 5 ml was drawn in one tube for a white cell count.

To separate aliquots of the patient's freshly drawn whole blood was added: a) pig anti-HIV-1 IgM serum, b) pig anti-HIV-1 type IgG serum, c) a nonimmune pig serum, and d) a nontreated control. The sera were inactivated by psoralen/UV treatment and added in a dilution of 1:50.

The tubes were placed on a rocker for 2 hours at room temperature, and then placed on a rocker at 37° C. for 20 hours. The tubes containing the whole blood were then transferred to an independent laboratory where the lymphocytes were isolated using Hypaque-Ficoll gradient centrifugation. The lymphocytes were then reacted with OKT4 and OKT8.

The white cell count was obtained and the lymphocyte populations were determined in a blind study on an Ortho Flow cytophotometer. Treatment of the infected lymphocytes with porcine anti-HIV-1 IgM resulted in a T4 cell increase from 196 per mm (16%) to 331 per mm (27%). Similarly, treatment with the porcine anti-HIV-1 IgG resulted in a T4 cell increase from 196 per mm (16%) to 68 per mm$^2$ (30%).

Thus, upon treatment with either of the porcine anti-HIV-1 IgM or IgG specific antibodies, the number of T4 cells doubled after about 22 hours of incubation. Since T4 cell depletion is regarded as a typical sign of approaching immune paralysis, effecting an increase in the serum T4 cell population of an AIDS patient would be of significant advantage in HIV-1 immunotherapy.

Example 7

Production and Formulation of Human Immunotherapeutic Composition

The development and production of an immunoglobulin product suitable for passive immunotherapy falls into three distinct stages: production of immuneserum; isolation and purification of immunoglobulin (preferably IgG) and formulation of the product for administration.

Production of Immuneserum

A Yorkshire mixed breed pig weighing between 150–200 pounds was used in this study. Following a general health check, the animal was kept under observation for approximately 7 days. During that period a 20 ccm blood sample was obtained, the serum of which was stored at −20° C. This serum sample serves as a 0-Time Control to monitor the immune response to HIV-1 antigens.

0.1 ml of HIV-1 viral lysate (1 mg/ml) was diluted with 0.9 ml of 1% SDS to 1.0 ml. Shortly before immunization this material was mixed either with 1.0 ml of Freund's complete adjuvant (for the first immunization) or with 1.0 ml of Freund's incomplete adjuvant (for all consecutive immunizations). Upon mixing of antigen with Freund's complete or incomplete adjuvant, the immunogen was injected into the pig.

At, 0-Time the pig was injected intracutaneously with 2 ml of the above immunogen at 2 or 3 different sites of the left neck. 24 hours later the pig was injected intracutaneously with 2 ml of the above immunogen (containing incomplete Freund's adjuvant) at 2 or 3 different sites of the right neck. 3 weeks later the pig was boosted with 2 ml of immunogen intracutaneously in the left neck. The booster was repeated 2 more times in intervals of 3 weeks.

The immune response was monitored on a biweekly basis by obtaining a 20 ccm blood sample and checking it in a Western blot assay as described above. Past experiments using this immunization protocol have shown that a satisfactory titer of anti-HIV-1 IgG is obtained after 60 to 90 days of immunization.

After it was determined that the HIV-1 IgG Western Blot profile of the individual animal was satisfactory, the animal was sacrificed by exsanguination. The blood was collected aseptically in sterile containers without anticoagulant. The volume of blood collected from a 150 to 200 pound pig ranges between 3 to 4 liters. Within 24 hours of collection, serum from the clotted blood was prepared by centrifugation. The amount of serum obtained per animal ranges between 1.3 and 1.8 liters. Thimerosal was added to the serum to a final concentration of 0.01%. Until further processing, the serum was stored in sterile containers at −20° C.

Isolation and Purification of IgG

For the purification of IgG a one step affinity purification step was employed using a novel gel (Avid AL, BioProbe, International, Tustin, Calif. 92680) specifically designed to bind immunoglobulin from mammalian species. The gel was prepared as a low molecular weight (less than 500 daltons) non-protein, non-carbohydrate, synthetic compound affinity ligand. Therefore, there is no protein ligand leaching. An important advantage of this synthetic ligand is its stability to prolonged acid or base treatment (a commonly used procedure for depyrogenation) and autoclaving (a commonly used procedure for sterilization). The ligand is also resistant to proteases. The affinity gel binds immunoglobulin G from pig under physiological saline (PBS) conditions. The bound IgG was eluted by applying a low pH buffer (acetic acid/sodium acetate, pH 3.0).

The protocol was designed in such a way that the total serum collected from one animal can be purified in one column run. The serum was diluted with 5 parts of sterile PBS (10 mM Sodium Phosphate buffer, 0.15M Sodium Chloride, 0.01% Thimerosal, pH 7.4). The diluted serum was filtered through a 0.45 micron filter and applied to the affinity chromatography column.

The column was packed with a sufficient amount of affinity gel to purify 300 ml of serum (diluted to 1.5 l in PBS). 4 ml of gel for every 1 ml pig serum have been found sufficient to purify IgG from the other serum fractions. The column is regenerated by washing it with 1.5 l of 20% Methanol in 1% acetic acid. Equilibration is carried out with 1.5 liters of PBS.

The diluted serum sample was applied to the column at a slow flow rate. The column was then washed with 5 liters of PBS or until the UV absorbance returned to a baseline value. IgG was eluted by passing 1.5–2 liters of sterile 0.05M Sodium Acetate (pH 2.8) through the column. The pH of the eluted immunoglobulin solution was then adjusted to 4.25 with sodium carbonate.

Fractions containing the IgG material were combined, and dialyzed against 0.01M Sodium Acetate, pH 4.25, using a hollow fiber ultrafiltration system with a MW-cut off (M.W.C.O) of 70,000. During the ultrafiltration process the IgG protein content was adjusted to a concentration of 50 mg/ml. The yield of purified IgG under the described conditions ranges between 10 and 15 mg/ml of unprocessed serum.

To ascertain that the IgG peak of the elution profile contains the antibody species reacting with HIV-1 antigens, fractions of the elution profile were tested in an HIV-1 IgG ELISA system. The experiments confirmed that the majority of the HIV-1 specific antibodies are retained in the IgG fraction. Quantification was accomplished by titering the purified IgG against an anti-HIV-1 IgG positive porcine standard serum. Titers were established for the core and the envelope proteins. Likewise, IgG subclasses were monitored for every IgG batch. Every IgG was monitored for purity using SDS-PAGE analysis. Previous experiments demonstrated that more than 95 percent of the protein has the electrophoretic mobility of gammaglobulin.

Formulation for Human Administration

The formulation for human administration, prepared as described below, is referred to herein by its laboratory designation, PASSHIV-1. The pH of the IgG preparation was adjusted to a value of approximately 4.25. It was found that decreasing the pH of gammaglobulin in solution markedly enhanced its monomeric content and stability, obviating the need for any chemical modification or enzymatic treatment (Schwartz, *Am. J. Med.* 83: (suppl. 4A) 46–51, (1987)). The concentrated IgG solution was formulated for clinical use as a sterile 5 percent solution (50 mg/ml) at approximately pH 4.25 in 10 percent maltose. The resultant product was checked for IgG content by cellulose acetate electrophoresis as well as by crossed immunoelectrophoresis. It should have greater than 95 percent IgG, less than 10% dimer aggregate and fragments, and IgA and IgM values less than 1% of the total gammaglobulin. Final checks include tests for sterility, toxicity and turbidity as well as pyrogenicity according to rules promulgated by the Bureau of Biologics. These rules related to general safety testing, sterility testing, and pyrogenicity testing which must be conducted before a drug may be used for treatment in humans. These tests were conducted at Biological Test Center, 2525 McGau Avenue, Irvine, Calif. 92714-5895.

Example 8

Human Immunotherapy

This example describes the medical history of a human volunteer who received intraveous doses of the PASSHIV-1 composition, as well as the results of the treatment.

Medical History

A 42 year old male United States citizen, with a past history of IV drug use and homosexual contacts, was first diagnosed in August 1988 with AIDS and pneumocystic pneumonia. The patient reported that in 1981 he had a period of fever, sore throat and palpable lymphnodes which persisted for a few days. He noted that this acute illness came shortly after he had shared needles for IV drug use. Furthermore, in the same period he contracted hepatitis. In 1984 he had a left ear infection which was treated with surgery and drainage.

Approximately 2 months prior to admission in 1988 he had experienced night sweats, nausea, vomiting, and diarrhea. A few weeks prior to this admission he had fever, decreased appetite, persistent dry cough and progressive shortness of breath. He also had lost 20 pounds during that period. Neurological status was normal. Physical examination at that time revealed a temperature of 38.5° C. and a few (less then 1 cm) auxiliary and inguinal lymphnodes. X-ray showed bilateral interstitial infiltrates moreso at the bases. A bronchoscopy was done and washings and a biopsy were taken. The washings were positive for honeycombing and the pathology on the biopsy was positive for pneumocystic carinii pneumonia (PCP). The patient improved markedly on IV pentamidine and completed a 14 day course without any complications. Blood cultures and stool cultures were negative. He was discharged with the following diagnosis: Pneumocystic carinii pneumonia with acquired immune deficiency syndrome.

He was started on AZT and remained on this drug until August 1989. At that time he became severely anemic. Since 1989 he had remained transfusion dependent. Dideozyinsone DDI treatment was started and was continued until March 1990 at which time the patient's blood revealed increased serum amylase. The patient remained transfusion dependent. He had been leukopenic (600–700 WBC/CU.MM) during the entire period since late 1989. During the same period the patient's platelets decreased profoundly. In October 1989 the patient developed PCP complicated with pneumothorax. In July 1990 the patient again developed PCP. During the last incidence of PCP he was noted to be $O_2$ dependent. He had a low oxygen saturation but he could be off $O_2$ after he was treated with pentamidine and pentamidine inhalations as well as monthly pentamidine shots. He appeared to remain low in $O_2$ saturation.

Clinical Treatment

The clinical treatment described below was conducted in Denmark. The PASSHIV-1 composition was allowed to be used in the country by the Danish Board of Health provided the PASSHIV-1 followed the patient from his home country, and provided, it would only be used in this patient.

Since the July 1989 admission the patient remained on multiple antibiotics such as Ethambutol, Rifampin, Coprofloxin, Klonopin, Fluconazole and Nystatin. He was treated with DHPG because of the presumed cytomegalovirus infection. However, this treatment had to be stopped because of his extremely low leukocyte count. He had been on erythropoietin since the summer of 1990 without any significant effect on his pancytopenic condition. He continued to have high fever and tachycardia and was constantly short of breath. The patient became kachectic and had to be maintained on intravenous nutrition via sic line at home. Since July he was severely disabled and bedridden.

In order to prepare the patient for flight transportation to Denmark, he was admitted to a United States hospital in mid-October 1990 and received 5 units of packed red blood cells and platelets which brought his hemoglobin from 4.0 mmol/L to 5.8 mmol/L.

After his admission to the Danish hospital his hemoglobin was again 4.0 mmol/L and his platelet count at approximately 20,000. His AIDS condition was considered severe (beyond Walter Reed Stage 6). He was somnolent and non-verbal. He was short of breath and had fever at approximately 38.8° C. Respiratory organs revealed fine crepitations, especially on the left side. He was emaciated, lethargic, glazed and kachectic. He had diarrhea but was not significantly dehydrated. He was maintained on parenteral nutrition.

A lymphocyte panel was performed. The patient appeared to have a WBC count of 700. The lymphocyte percentage was approximately 12.8%, or 90 cells per CC.MM (normal range being approximately 480 to 5,600 per CC.MM). His total T-subsets were 71% (approximately 340 cells). His B lymphocytes were 1% (approximately 5 cells). His T4 cells were 1% (approximately 5 cells, with the normal range being approximately 400 cells or more). His T4 cells were 67% (approximately 322 cells). It was not possible to get a T-subset count after treatment. The patient was attached to a Cardiocap which constantly monitored his pulse, ECG, blood pressure, temperature and oxygen saturation during the PASSHIV-1 infusion.

On day 1, one gram of PASSHIV-1 was diluted in 250 ml of human albumin (5%) (Immuno, Austria). The flow rate was controlled by using a dose pump. During the first hour the patient was infused with 48 ml of albumin diluted PASSHIV-1. The patient showed no signs of side effect (he already had a fever at the start of the treatment). The flow rate was then set at 72 ml per hour for the next hour. No side effects were noted. The flow rate was then raised to 96 ml per hour. It was noted that during the course of the infusion the patient exhibited significantly less shortness of breath. At the same time it was noted that his $O_2$ saturation increased from 93% to 96% which is considered a significant improvement of his oxygen saturation. It was noted that his platelet count dropped considerably during the first day of treatment. The patient was treated with platelet transfusions. Platelet transfusions were continued on consecutive days of treatment with PASSHIV-1.

On day two of treatment, 2 grams of PASSHIV-1 were diluted in albumin (2 grams in 230 ml albumin). The patient was infused starting with a low flow rate of 48 ml per hour. After one hour the flow rate was increased to 72 ml per hour.

A temperature peak after 2 hours of infusion was successfully treated with 650 mg of Tylenol p.o.

Since the patient had a history of fever development from infused blood and blood products it was impossible to determine whether the fever top was due to PASSHIV-1 or to the blood products given. However, even when increasing the flow rate of PASSHIV-1 to 92 ml per hour, the body temperature did not increase. No other side effects were noted during the second day treatment.

A white blood cell count was done prior to the start of infusion and after the end of infusion. It was noted that besides a drop in the platelet count (which could be controlled by infusion of platelets) the lymphocyte count was markedly lower at the end of the infusion as compared to the start of the infusion. On day 2 the total white blood cell count started to show an increase at a time where the lymphocyte fraction still showed a significant decrease at the end of the second treatment day. It was also found that the monocytes showed a decline at the end of each treatment day whereas the granulocytes entered a proliferative phase. In the evening (approximately 2 hours post treatment) the patient was noted to be lethargic and febrile. He was given I.V. hydration and Lasix because of the possibility of toxic loading due to cell lysis. The forced hydration had a favorable effect on the patient's general condition within 2 hours.

The treatment protocol for day 3 recommended 3 grams of PASSHIV-1. However, the platelet count had decreased to approximately 5,000 with the first 2.3 grams of treatment. The infusion was stopped and 6 units of platelets were infused which brought the platelet count up to 20,000. The patient had a temperature of approximately 38.0° C. when the infusion was started. The fever was treated with 650 mg of Tylenol which, after 30 to 40 minutes, brought the temperature down to normal. The flow rate of the PASSHIV-1 (2 grams in 230 ml of human albumin) was increased to a flow rate of 96 ml per hour without producing any side effects other than a minor rise in temperature with a peak at 38.0° C. The leukocyte count continued to show a slight increase to 1000 cells per CC.MM. The lymphocytes and the monocytes continued to decrease significantly. The increase in total WBC was due to the increase in granulocytes.

Blood smears were prepared at the start and at the end of each PASSHIV-1 infusion from day 3 through 7. Prior to day 4 treatment the patient was transfused with 4 units of packed red blood cells in the early AM hours of day 4 since his hemoglobin value was approximately 5.5 mmol/L at the end of day 3.

On day 4, three (3) units of platelets were infused prior to the start of PASSHIV-1 infusion. The patient developed a fever of 38.5° C. at the start of the PASSHIV-1 treatment. The rise of temperature coincided with the ending of the platelet transfusion. The PASSHIV-1 infusion was administered at 2 grams in 230 ml human albumin and 1 gram in 100 ml albumin. The temperature rise was successfully treated with 650 mg of Tylenol.

The flow rate of PASSHIV-1 was gradually increased, as done previously, to a rate of 96 ml per hour. Interestingly, the patient started somewhat higher in $O_2$ saturation and after 30 minutes of infusion his oxygen saturation leveled off at 96–98%. 3 units of platelets were given when starting on the last 1 gram of PASSHIV-1. The patient again developed fever. It was concluded that the temperature increase was due mainly to the transfusion of packed red blood cells as well as to the platelet infusion rather than to the infusion of PASSHIV-1.

The patient's leukocyte count rose to 1200 whereas the lymphocyte and monocyte count dropped. The platelet count did not fall drastically on this day as compared to the previous treatment days. In order to rule out any possible imminent disseminated intravascular coagulation (DIC) plasma fibrinogen and plasma antithrombin 3 were given over the next days. The values showed actually slightly elevated values negating any concern of a DIC. That evening the blood smear showed appearance of several polynuclear bands and a few metamyelocytes, indicating an activation of the patient's bone marrow. Approximately 2 hours post infusion the patient again had a period where he was weak, tired, and lethargic.

On day 5, the patient was given a "resting" day. On the evening of that day erythroblasts (immature red blood cells) were appearing in the peripheral blood indicating an active red blood cell producing bone marrow in the patient.

On day 6, the scheduled PASSHIV-1 treatment was given at a dose of 4 grams, split up into 2×2 grams each in 230 ml of human albumin. Prior to and during the PASSHIV-1 infusion the patient received 2×3 units of platelets. The patient's temperature rose to 39.7° C. after infusing the second batch of platelets. The temperature decreased upon Tylenol administration and ice packs. No adverse reaction other than the rise in temperature was noted. Pulse and blood pressure were within the normal range during the entire infusion of PASSHIV-1.

Several hours after treatment the patient was noted to have a resistant gurgling cough. Thick secretions were removed from his mouth and nose. The patient progressively developed shortness of breath and Rx basalar rhonchi were heard. The patient received endotracheal suction but secretions were scant; his color became pale. The patient received nasal intubation with repeated suction. The $O_2$ saturation fell but was recovered with a brief period of bagging. The patient received 40 mg Lasix and 100 mg Solucortef (Cortisone) I.V. His color and oxygenation improved. He was extubated with stable vital signs (blood pressure 125/82, pulse rate 154). The patient received more diuretics (20 mg Lasix I.V.) and 100 mg Solucortef I.V. in the early AM.

His color and oxygenation improved quickly and he was extubated with stable vital signs (blood pressure 125/82, pulse rate 154). His color and oxygenation improved during the evening hours and at 12 AM $O_2$ was at 94%. The patient's blood pressure and pulse-rate had not shown significant changes, especially no signs of a fall in blood pressure were noted. Furthermore, no changes were evident in the ECG. At 12 AM that night hemoglobin was 7.1 mmol/L, leukocyte count had risen to 1,800 per CC.MM; and platelets were 14,000.

The next morning the patient's leukocyte count was 2,800 per CC.MM. Hemoglobin was stable at 7.1 mmol/L. His lymphocyte count did not show any significant drop after the last treatment day and the lymphocytes increased dramatically from approximately 170 cells to approximately 820 cells per CC.MM. Additionally, his monocytes did not show any decrease after the last day of treatment and the next day they had increased to approximately 170 per CC.MM. His granulocytes increased to 1,750 per CC.MM. The patient received more diuretics (20 mg Lasix I.V.) and 100 mg Solucortef I.V. in the early AM.

The patient's general condition had improved remarkably. He was sitting up in bed alert, energetic, and had no shortness of breath. He was constantly talking and discussing, laughing and joking all day. He wanted to get up in a wheel chair and was wheeled around the halls of the hospital. He was highly interested in his surroundings. His blood smear still showed a left skewed picture, with more immature red and white blood cells, but with an otherwise normal distribution.

After a short conference with the patient, it was decided that he should be transported back to the U.S. by flight the following day. The main reason for this decision was that the local public hospital and blood bank had been uncooperative in its service to this patient by showing decided unwillingness to provide further T-cell subset investigation as well as serving the patient with blood products. Actually on treatment day 5 the blood bank decided not to send more platelets for the patient since the hospital at which treatment was being administered was a private hospital. It was recognized that platelets would be needed during the last day of treatment which at that time was already in progress when we were denied more platelets in spite of all attempts to persuade the local hospital.

Approximately 6 days after his admission to a hospital in the United States the patient died from pneumonia. It was found that he had a major infiltrate in his left lung which, when comparing X-rays from the hospitalization prior to the transfer of the patient to Denmark, showed a lung infiltrate in the same area.

General Clinical Chemistry

FIGS. 1–5 represent a summary of the patient's general clinical chemistry over the treatment period. FIG. 1 represents data from white blood cell count and blood smears. During the first four days of infusion with PASSHIV-1 the patient's lymphocytes and monocytes declined significantly and rebounded the following morning. The polynuclear leukocytes increased during the same period. The total number of WBC started to increase slowly to 1200. From the third day of treatment onwards the blood smears showed a more immature picture, with appearance and increase of BANDS. On the last day of treatment the total WBC increased significantly. Lymphocytes as well as monocytes did not show any signs of decrease. The following day the total WBC count was at 2800. The lymphocytes had increased dramatically. The granulocytes as well as the monocytes also showed an increase to near lower normal values. The blood smear showed a left skewed more immature picture with the presence of a few promyelocytes, metamyelocytes, and an increase in BANDS. The initial decrease in lymphocytes on the first 4 days of treatment might be evidence of lymphocyte death (monocyte death) due to treatment. On the fifth day ("resting day") no decrease in lymphocytes or monocytes was noted. The increase in WBC coincided with a profound decrease in circulating p24 core.

Figure 2:
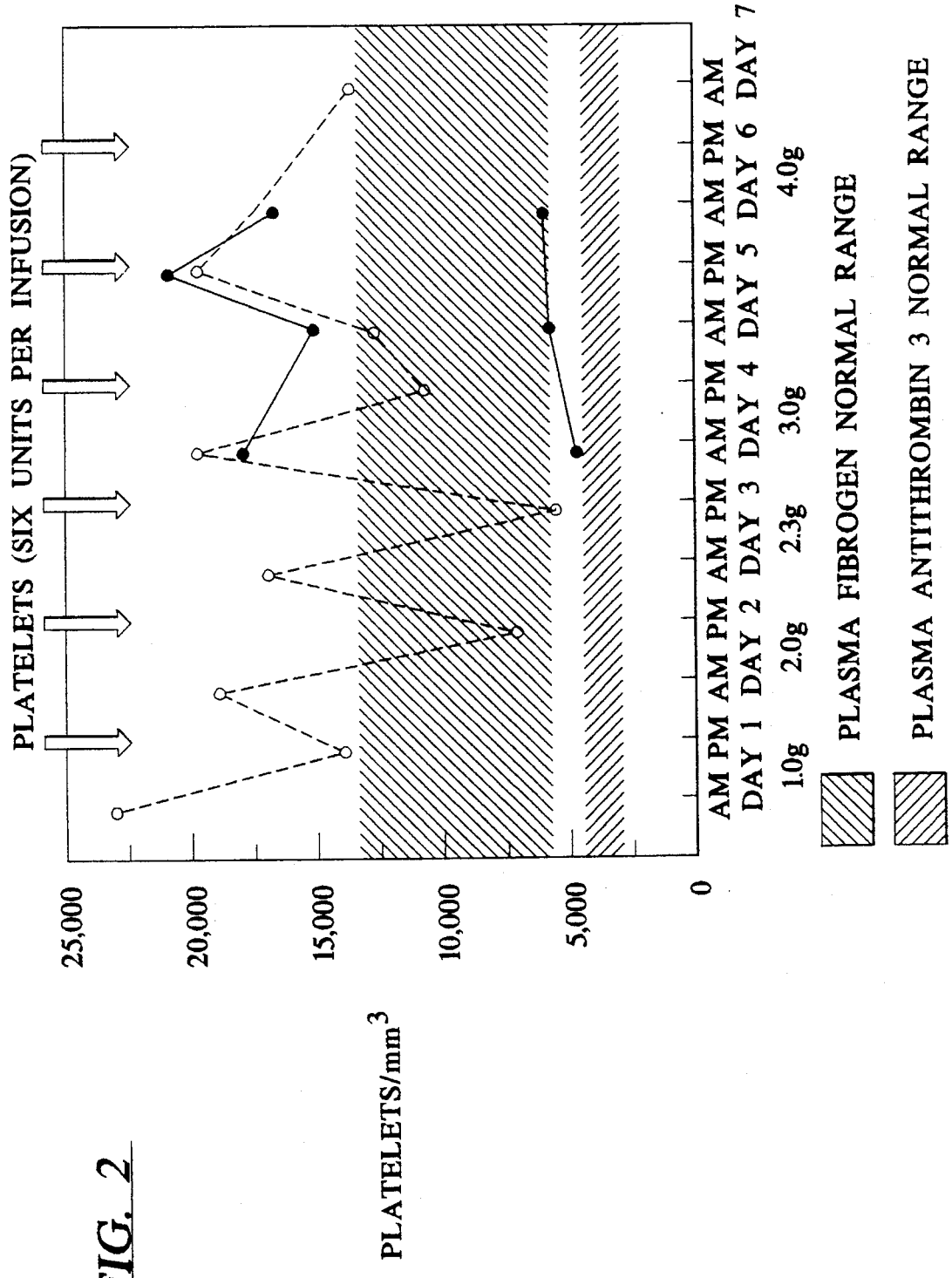
FIG. 2 is a diagram representing data relating to platelets and coagulation factors in an HIV-1 infected individual treated with an immunotherapeutic composition.

FIG. 2 represents data relating to platelets and coagulation factors. The patient was platelet transfusion dependent for several months prior to admission to the Mermaid Clinic. His platelet count prior to PASSHIV-1 treatment was approximately 24,000. The patient received 6×6 units of single donor platelets during his admission to Danish Hospital. His platelets declined at each treatment course with PASSHIV-1. However, the decline was less pronounced with the last 4 gram dose. His plasma fibrinogen and plasma antithrombin 3 was slightly over normal. There were no signs of imminent disseminated intravascular coagulation. The uptake of platelets during treatment may, among other reasons, be due to lysis of infected endothelial cells resulting in vascular microlesions.

Figure 3:
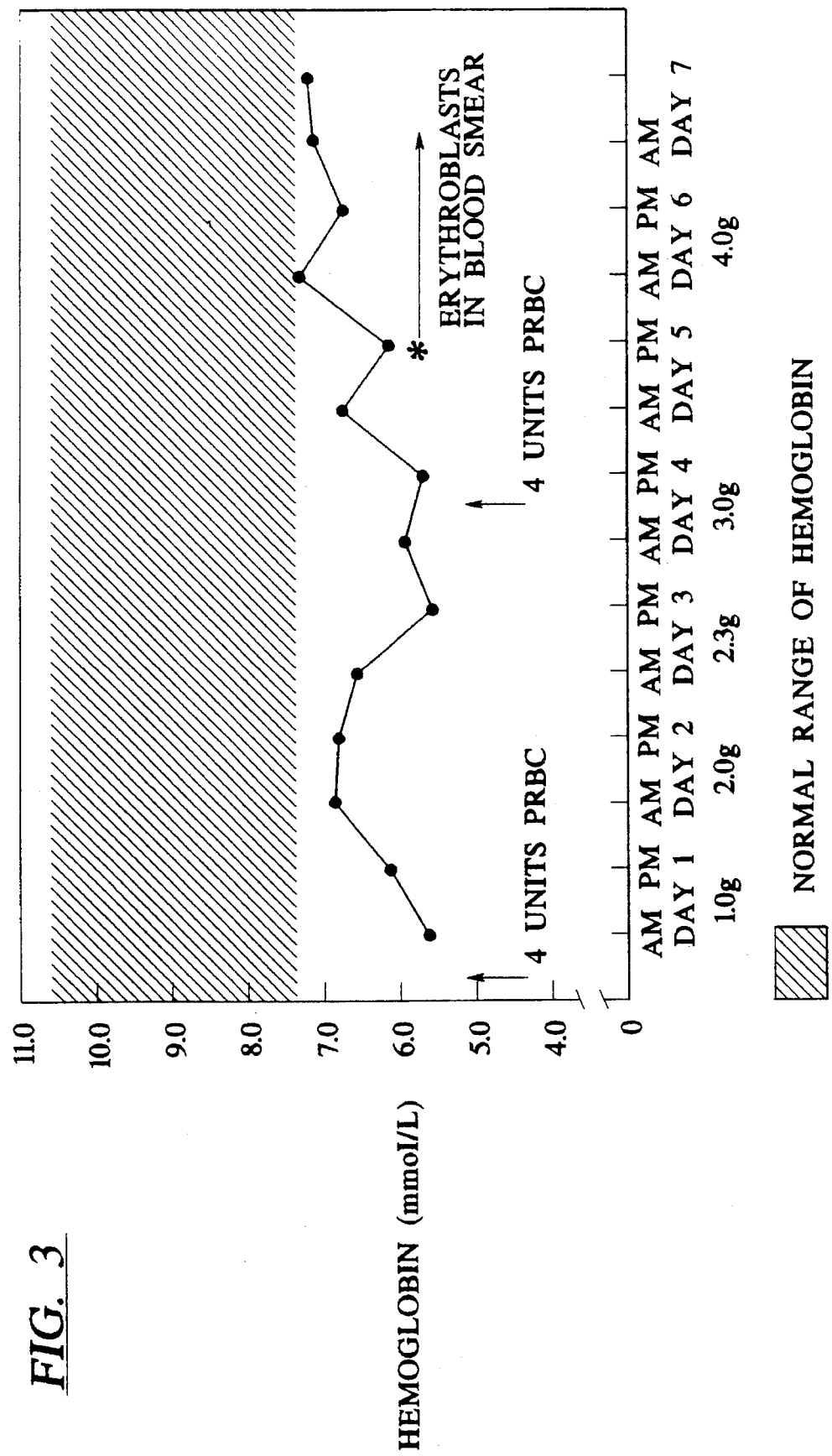
FIG. 3 is a diagram representing hemoglobin levels in an HIV-1 infected individual treated with an immunotherapeutic composition.
Figure 4:
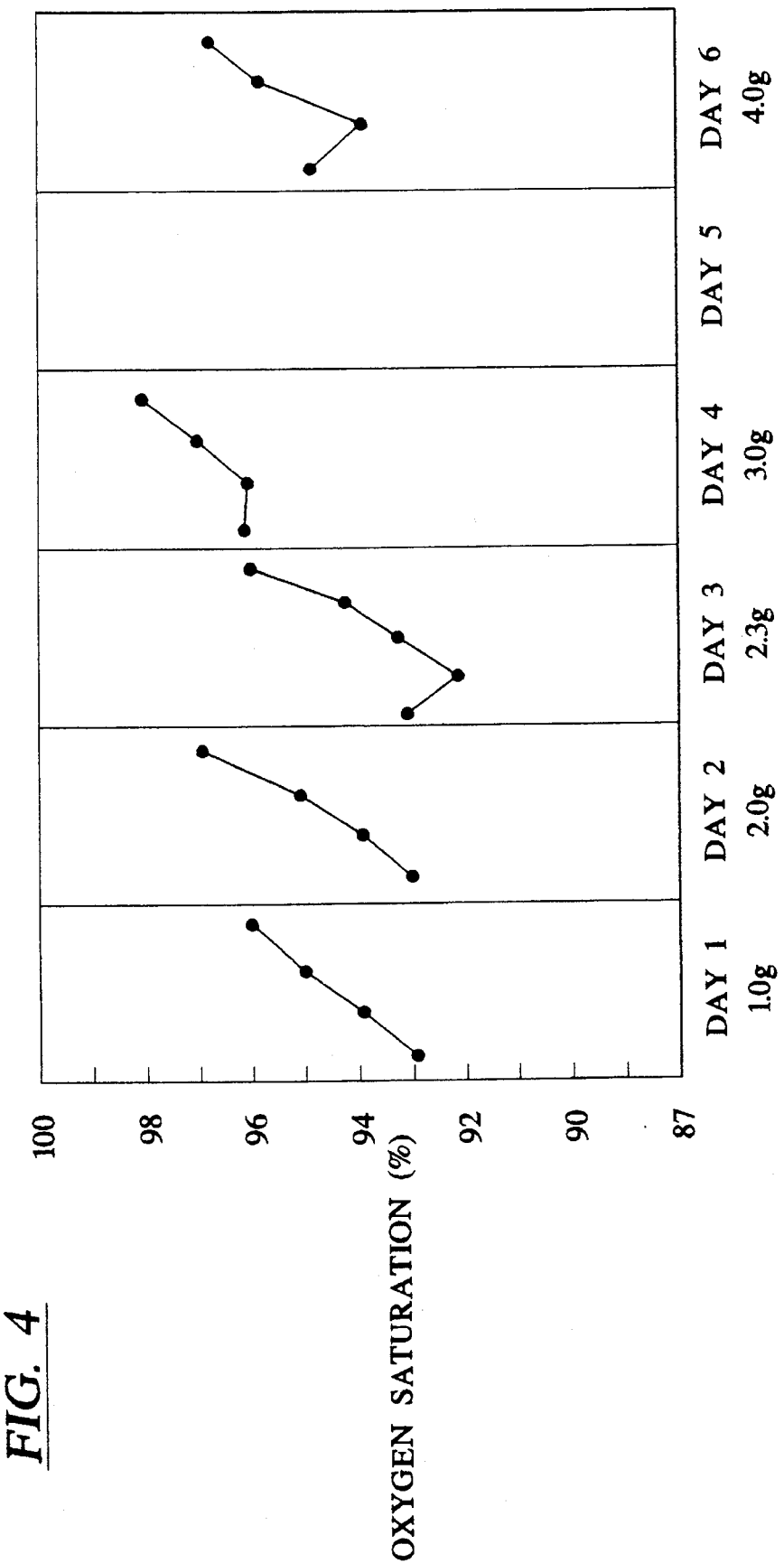
FIG. 4 is a diagram representing oxygen saturation data in an HIV-1 infected individual treated with an immunotherapeutic composition.

FIG. 3 represents hemoglobin determinations during the treatment period. On admission to the Danish Hospital the patient had a hemoglobin value of 4.4 mmol/L. He had been transfused in the U.S. prior to transport which raised the hemoglobin value to 5.8 mmol/L. Prior to treatment with PASSHIV-1 and after treatment on day 4 he was transfused with 4 units of PRBCs. On day 5 he showed erythroblasts in his peripheral blood. Since that time he started to produce his own red blood cells. This phenomenon coincided with decreased concentrations of circulating p24 core.

Figure 5:
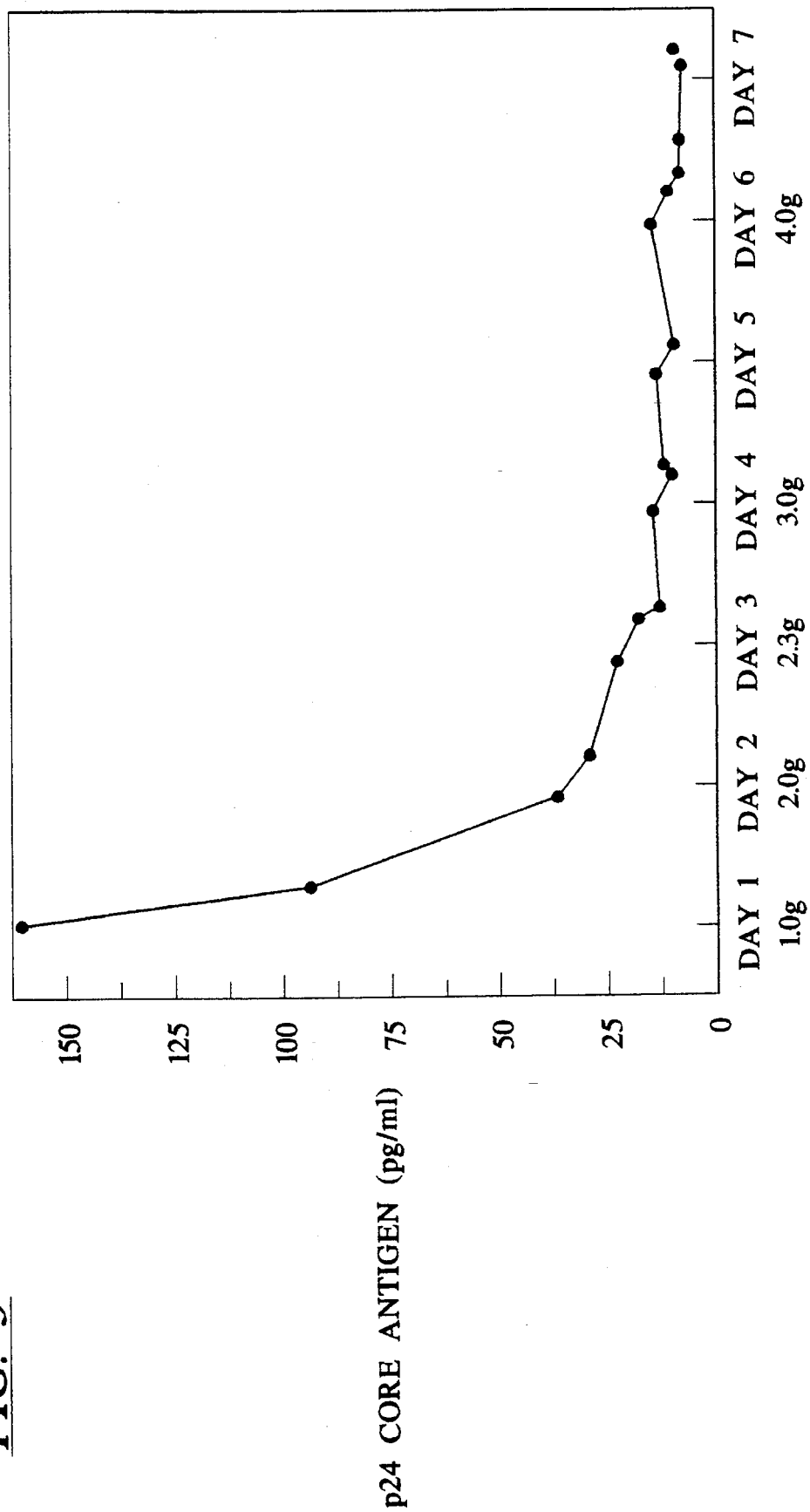
FIG. 5 is a diagram representing p24 core antigen clearance in an individual treated with an immunotherapeutic composition.

FIG. 5 represents oxygen saturation data from the patient over the course of treatment. The patient had an oxygen saturation of 93% prior to the start of PASSHIV-1 treatment. It was noted that during the infusion his oxygen saturation improved significantly up to 96–98% on the days of treatment. At the moment there is no explanation for this phenomenon which was beneficial to the patient. The $O_2$, $CO_2$, pH status, etc. in blood obtained by arterial puncture were measured. There was no significant difference in $CO_2$ and pH during treatment. Consequently, the increase in saturation was not due to hyperventilation. Furthermore, it was noted that the patient's respiration frequency was slower during treatment compared to the start of treatment indicating no signs of hyperventilation.

The Western Blot profile of the patient over the course of treatment was tested twice daily. Prior to administration of PASSHIV-1, the Western Blot shows no detectable gp48 or p18 bands, but did show a weak p24 band. The Western Blot results showed a generally increasing p18 band intensity over the course of treatment, consistent with an accumulation theory. As progressively more porcine antisera is administered, the anti-p18 antibody accumulates in the serum resulting in increasing band intensity.

However, the same trend was not observed with the anti-gp48 and anti-p24 core antibodies. The anti-gp48 antibodies were not detectable in the assay, even on day 7. Clearly this antibody was being delivered in high titer to the patient. The most likely explanation for the absence of the gp48 band in the Western Blot is that the antibody was being utilized by the patient. That is, the gp48 specific antibody was binding to cells infected by the virus. It is presumed that when the anti-gp48 saturation point was reached (i.e. when a substantial portion of the anti-gp48 target molecules were complexed with the antibody), the Western Blot would reveal a trend toward accumulation of the anti-gp48 antibody in the serum of the patient.

This, in fact, appears to have occurred with the p24 core antibody. A weak p24 band is present in the patient's serum prior to PASSHIV-1 administration. The intensity of this band remained relatively constant through mid day 4. This is to be contrasted with the p18 band intensity which increased progressively from the start of treatment through mid-day 4. Thus, an explanation consistent with this data is that through mid-day 4, the anti-p24 antibody infused to the patient was binding substrate in a linear manner. After mid-day 4 through the duration of treatment, the anti-p24 band increased in intensity as would be expected if the saturation point had been reached.

Independent and dramatic support for this explanation is shown in FIG. 5. FIG. 5 shows the results of an ELISA assay which was used to monitor the concentration of HIV-1 p24 core antigen in the patient's serum. As can be clearly seen, the concentration of p24 core antigen dropped precipitously following PASSHIV-1 administration. The Western blot profile, referred to above, correlates perfectly with the saturation theory and Western blot data.

Figure 7:
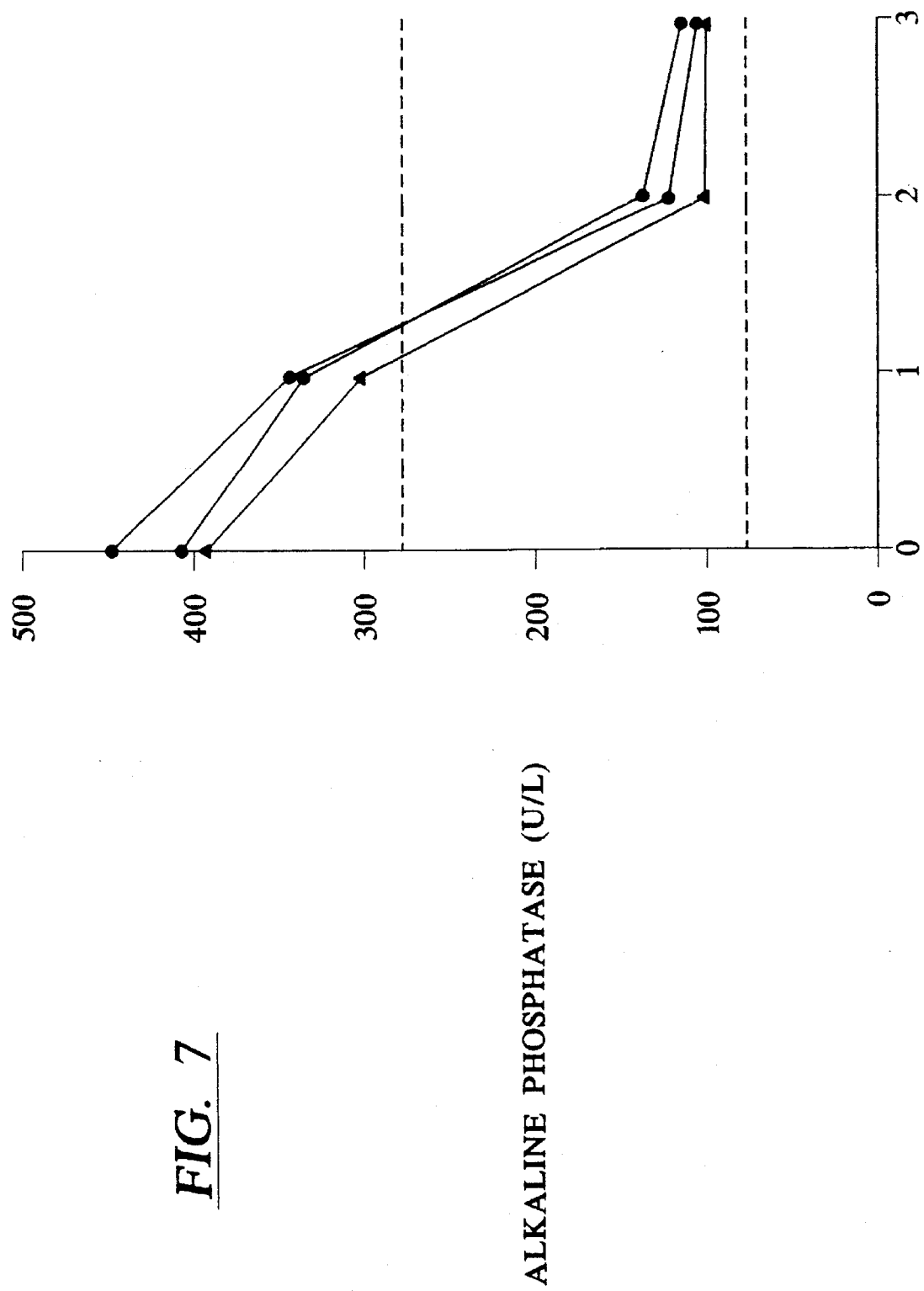
FIG. 7 is a diagram of alkaline phosphatase activity in patients with initially abnormal values. Serum alkaline phosphatase is shown before therapy (0) and at weeks 2, 8, and 12 post-therapy. Normal range ( - - - )

FIG. 7 represents levels of circulating p24 core during the treatment period. The HIV-1 p24 core antigen testing has been performed on Dupont's HIV-1 p24 Core Profile ELISA. The ELISA test has been performed on two separate days. The test results are consistent and reproducible. Prior to the start of PASSHIV-1 treatment (baseline) the patient serum had a concentration of 157.6 pg/ml of HIV-1 p24 Core antigen. At the end of the first infusion with 1 gram of PASSHIV-1 the concentration decreased to 92.1 pg/ml. On day 2 prior to PASSHIV-1 infusion the p24 antigen had fallen to 36.6 pg/ml. At the end of the Day 2 treatment with 2 grams of K053 IVIG, the concentration decreased to 28.9 pg/ml. At the end of the Day 3 infusion with 2.3 grams of PASSHIV-1, the concentration decreased to 15.5 pg/ml. At the end of the Day 4 infusion with 3 grams of PASSHIV-1 the concentration decreased to 13.9 pg/ml. The patient "rested" the fifth day; the values on that day were 15.3 in the morning and 12.2 pg/ml in Mid-day. At the end of Day 5 treatment (sixth day) the value was at 10.5 pg/ml. The last day results (one day post infusion) showed values between 9.9–10.5 pg/ml. The threshold was calculated to be approximately 5 pg/ml.

Example 9

Identification of Anti-gp48 Antibodies in Human Patients

A first patient (Patient No. 1) was a female kidney dialysis patient who had received numerous blood transfusions and had had one unsuccessful kidney transplant. The patient had no AIDS or ARC symptoms. The patient seroconverted with the appearance of a gp 48 band on a Western Blot assay employing a high-purity, solubilized HIV-1 lysate (HIV-1 lysate, Western Blot Grade, ProtaTek, Inc.). The presence of the gp 48 antibodies was not independently confirmed by Western Blots on other more impure lysates.

A second patient (Patient No. 2) was a 23-year old female IV-drug user who was tested prior to an induced abortion. The patient had no signs of AIDS or Aids-Related Complex (ARC). She died 14 days after induction of the abortion from disseminated intravascular coagulation during profuse uterine bleeding. The serum sample from the patient was HIV-1 Ab ELISA positive; upon Western Blot assay, gp 48 antibodies were resolved. After further Western Blot assays employing different HIV-1 lysates, the presence of the anti-gp 48 was independently confirmed.

A third patient (Patient No. 3), a female, had received numerous cryoprecipitates and Factor VIII products because of a yon Willebrands bleeding disorder for several years. The patient had not developed any AIDS or ARC symptoms. She was found to be HIV-1 ELISA positive, and anti-gp 48 was detected on Western Blot assay. The Western Blot assay of serum from this patient shows protein banding at gp48 and 160.

A fourth patient (Patient No. 4), a male suffering from metastatic carcinoma, had received multiple blood transfusions for a number of years. He had not developed any AIDS or ARC symptoms. His blood was found to be HIV-1 ELISA positive, and the presence of gp 48 was identified by Western Blot.

A fifth patient (Patient No. 5) was a 30-year old female who had no overt symptoms when tested for HIV-1 antibodies. She was pregnant (first month, first trimester) and had previously used IV drugs under unhygienic conditions. Conception had occurred with a homosexual male who was HIV-1 positive, thereby prompting the test. The patient's blood was found to be anti-gp 48 positive.

A sixth patient (Patient No. 6), a female, was also treated; her blood was classical HIV-1 antibody positive, displaying banding at p24, gp41, p53, p55, p64, pg120 and gp160.

A conclusion consistent with the findings reported above is that HIV-1 infected individuals producing anti-gp48 antibody species tend to have a high degree of resistance to the onset of viral infection symptoms.

Example 10

Blocking Binding Sites of Other HIV-1 Antibodies with Anti-HIV-1

The effect of anti-HIV-1 on the resolution of other protein constituents of HIV-1 was determined by Western blot assays employing strips pretreated by absorbing anti-HIV-1 sera thereon.

Absorption of Anti-HIV-1 from Patient No. 4

Serum from the patient with yon Willebrands disease (Patient No. 4) was diluted 1:100 in PEG 8000 (5% w/v) in PBS-Tween 20 in 5% w/v nonfat milk proteins. Three ml of the diluted serum was added to HIV-1 Western Blot strips prepared as described herein and incubated for 2 hours in a slotted tray at room temperature with gentle agitation. As a control, human HIV-1 antibody negative serum was diluted in the above-described buffer. Three ml of the diluted serum was added to HIV-1 Western Blot nitrocellulose strips in a slotted tray and incubated for 2 hours at room temperature with gentle agitation.

Following incubation, the Western Blot strips were washed 4 times (1 minute each time) with PBS-Tween buffer to remove excess unbound protein. The strips were then incubated with sheep antihuman IgG (Calbiochem #554826) at a dilution of 1:500 in PBS-Tween buffer. 3 ml of the diluted antibodies were added to each strip in a slotted tray and incubated at room temperature for 2 hours with gentle agitation. The strips were then washed 4 times (1 minute each time) to remove excess unbound sheep proteins.

The strips were then incubated with:

(i) HIV-1 Western Blot Positive serum (ProtaTek HIV-1 Western Blot Lysate Grade) which resolved the following HIV-1 Ab bands: p18, p24, p31/33, gp 41, p53 (p51), p55, p64 (p66), gp 120 and gp 160. The test serum was diluted 1:20 in PEG-PBS-Tween-5% w/v nonfat milk protein buffer;

(ii) Serum from Patient No. 1, diluted 1:20 in the last-mentioned buffer;

(iii) Porcine serum immunized with HIV-1 (gp 48 positive) diluted in the above buffer; or (iv) Serum from Patient No. 6, diluted 1:20 in the above buffer.

All the Quick Western Blot strips (both those pretreated with the serum from Patient No. 4, and those strips coated with the HIV-1 negative serum) were incubated in the tray at room temperature for 15 minutes with gentle agitation. The strips were washed with PBS-Tween 4 times (1 minute each time) to remove excess unbound proteins. Goat anti-human IgG horseradish peroxidase conjugate (ProtaTek, Lot M) was diluted 1:500 in PBS-Tween. 3 ml of the diluted conjugate was added to the strips and incubated for 15 minutes at room temperature with gentle agitation. The strips were washed 4 times (1 minute each time) in PBS-Tween and once (1 minute) in PBS alone.

3,3'-diaminobenzidine tetrahydrochloride dihydrate (DAB) (Aldrich Chemical Co., Milwaukee, Wis.) was diluted in PBS containing hydrogen peroxide (50 mg DAB/100 ml) for use as a substrate (chromogen). 3 ml was added to each strip and color reactions were obtained when incubated with the strips for 10 minutes with gentle agitation. The strips were then studied for protein bands.

It was found that gp 41 and gp 120 were not bound to the strip pretreated with the porcine anti-gp 48 and tested with the HIV-1 Ab positive serum [(iii) above], gp 160 being the only visible envelope protein. No other bands were altered. However, the strip revealed a weak gp 48 binding (as contrasted with the strip tested with the anti-gp 48 serum from Patient No. 1 [(ii) above]. Another protein, gp 90, which is rarely seen as a diffuse band on HIV-1 Ab positive strips (this protein is known to be a highly glycosylated protein reported to be related to the HIV-1 envelope), became more dense and visible on anti-gp 48 pretreated strips.

Strips pretreated with the negative serum had all the HIV-1 specific bands which exhibited binding on the strips tested with HIV-1 antibody-containing serum. Thus, Quick Western Blot strips pretreated with HIV-1 Ab negative serum do not prevent HIV-1 Ab specific proteins from appearing.

The strips pretreated with anti-gp 48 serum and tested with anti-gp 48 sera from other patients and from the HIV-1 Ab positive pig (showing the presence of the gp-48 band) showed binding of gp 48. Therefore, HIV-1 Ab positive serum containing all HIV-1 specific bands, including gp 120 and gp 41 on strips which have been pretreated with anti-gp 48 serum, do not bind gp 160 and gp 41.

The binding of anti-gp 48 to pretreated Western blot strips apparently blocks binding sites for antibodies (HIV-1 Ab) of envelope proteins gp 160 and gp 41 and, to a certain extent, gp 120, which may be part of or the entire binding site for anti-gp 120 and anti-gp 41.

Absorption of Porcine Anti-gp 48

Porcine serum containing anti-gp 48 was diluted in PEG 8000, 5% w/v in PBS-Tween with 5% w/v nonfat milk proteins to a dilution of 1:50. HIV-1 Quick Western Blot strips were incubated with the diluted porcine serum (3 ml per strip) in a slotted tray for 2 hours at room temperature with gentle agitation, and then washed. The strips were reincubated with sheep antihuman IgG (Calbiochem #554826) at a dilution of 1:500 following the same procedure described in part (a) above.

The pretreated strips were subjected to assay by Western blot. A first strip tested an HIV-1 Ab positive serum sample. A second strip was incubated with anti-gp 48 serum from Patient No. 1, an third strip with porcine HIV-1 positive serum, and a fourth strip with anti-gp 48 serum from Patient No. 6. Nonpretreated HIV-1 Western blot strips were tested with the same serum samples.

As in the case of the pretreatment of the strips with anti-gp 48 human serum described above, the porcine anti-gp 48 serum pretreated strips did not bind gp 160 and gp 41 from the HIV-1 Ab positive patient (whose serum blotted all the known HIV-1 proteins, including gp 160, 120 and gp 41, on the untreated strip). Thus, the porcine anti-gp 48 serum, like the anti-gp 48 human serum, neutralizes or prevents binding of antibodies to gp 160, gp 41 and, to a certain extent, gp 120.

Based on the preceding experiments, it has been found that solubilized HIV-1 lysate produces antibody to gp48 in pigs, which prevents antibody binding of antibodies to gp160 gp41 and, to a certain extent, gp120.

Example 11

Assay for Detection of HIV-1 Infection Pre-Immune Response

Blood obtained from a healthy individual was incubated overnight with intact HIV-1 virus under conditions appropriate for infection of CD4 bearing cells in the blood. Lymphocytes were isolated from the blood and the lymphotcytes were incubated with anti-HIV-1 antibodies, prepared as described above, for 30 minutes at 4° C. Also included in the 30 minute incubation mixture was an FITC conjugated anti-porcine secondary antibody. Specific binding of the fluorescent antibody to infected cells was clearly detectable.

Example 12

Fourteen HIV-1-infected individuals were treated for 5–7 days with intravenous infusions of highly purified PASSHIV-1 (>95% pure). Two of the 14 patients were retreated 3 months later with hyper-immune immunoglobulin of this invention (PASSHIV-1) for an additional 5 days to evaluate side-effects from retreatment with porcine immunoglobulins.

The results, which can also be found in the December 1992 journal of AIDS, Vol. 6, No. 12, pp. 1457–64, are as follows. Ten of the patients had no side-effects from PASSSHIV-1 therapy. Three patients experienced transient urticarial eruptions, which responded to antihistamine administration and did not require discontinuation of therapy. One patient, who received concomitant administration of human gammaglobulin, experienced serum sickness (type 3 hypersensitivity reaction). All patients demonstrated a significant improvement in fatigue (100% response), weight (all those with previous weight loss gained weight), fever (100% response), polyneuropathy (100% response), bronchitis (100% response), candidiasis (100% response), diarrhea (100% response), and dermatitis (100% response). One out of the five patients with Kaposi's sarcoma demonstrated >50% improvement. Mean CD4+ cell counts in the group rose from $143\pm263$ to $234\pm323\times10^6/1$ 4–6 months following completion of therapy (P=0.013, paired Student's t-test); CD4+ cell counts in the group rose twofold in six individuals. p24 antigen, present in four patients, was negative following therapy in all patients. Other laboratory parameters that responded to therapy included: platelet counts (71% response), leukopenia (57 response), elevated lactic dehydrogenase (100% response), and elevated alkaline phosphatase (100% response). PASSHIV-1 was well tolerated by HIV-1-infected individuals and appears to be efficacious in ameliorating some of the clinical aspects and symptoms of HIV-1 infection indicates that anti-HIV hyperimmune porcine immunoglobulin appears to be well tolerated by HIV-infected individuals. Results of this study also indicate that these individuals benefitted from such therapy.

Patients and methods

Hyperimmune porcine immunoglobulin

Yorkshire mixed breed pigs were immunized with HIV-1 lysate containing env (gp160, gp120, gp41), gag (p24, p55), and pol (p66, p53) purchased from Organon Teknika (Durham, N.C., USA; patent pending). The porcine anti-HIV-1 hyperimmune serum was heat-inactivated, adjusted to 35% ammonium sulfate to precipitate immunoglobulins, redissolved in phosphate-buffered saline, subjected to affinity chromatography using an Avid AL gel column (Bioprobe International, Tustin, Calif., USA) according to the manufacturer's instructions, and sterilized by filtration through a 0.2 μm filter (Gelman Sciences Inc., Ann Arbor, Mich., USA). This process yields a highly purified immunoglobulin preparation, with the immunoglobulin G (IgG) fraction constituting >95% of the proteins. The hyperimmune globulins have been characterized for antibody titer, specificity, HIV-1 neutralization titer, antibody dependent cytotoxicity, and syncytium formation inhibition. OSTHER K., KELLERMANN G, UGEN K. E., WILLIAMS W. V., WEINER D. B.: Protective humoral immune response to human immunodeficiency virus induced in immunized pigs, *Hybridoma* 1991, 10:673–683; CAMPBELL W. B., HUGHES M. J., OSTER K.: A rapid screening test for HIV-1 antibodies: application to biological studies on human tissue, *Life Sci* 1991, 48:347–353; OSTHER K., KLINTMALM G.: The quick Western blot, a novel transportable 50-minute HIV-1antibody test. Application in organ procurement for transplantation, *Transplantation* 1989,47:834–838. The immunoglobulin product is formulated as an intravenous immunoglobulin and designated PASSHIV-1 for brevity. Each ml contains 50 mg protein, of which 95% has the electrophoretic mobility of γ-globulins. Each individual batch of serum has been tested in human, porcine and monkey cell lines for evidence of live virus and found to be non-reactive. Each batch of PASSHIV-1 has been tested for general safety, pyrogenicity, and sterility by an independent Food and Drug Administration-approved laboratory (Biological Test Center, Irvine, Calif., USA).

Patients

The initial study group consisted of 14 HIV-infected individuals. Twelve were male and two female. Six patients were in stages 1–3 and eight in stages 4–6 of the Walter Reed staging system. Patient characteristics upon entry to this study are shown in Table 12. Mean age of men treated with PASSHIV-1 was 40.8 years (range, 23–48 years). The two women treated with PASSHIV-1 were 29 and 30 years old.

discontinued both zidovudine and ddC. One patient continued to take low-dose zidovudine throughout PASSHIV-1 therapy. Low-dose zidovudine was stopped in another patient approximately 1 month after second-cycle PASSHIV-1 treatment because of side-effects. The fourteenth patient commenced ddI alone, but was unable to tolerate treatment because of side-effects.

In summary, at the time of PASSHIV-1 treatment four patients were on zidovudine, three were on combined zidovudine and ddC, and one was on ddI. Four patients were not on any of these drugs during PASSHIV-1 treatment. All patients received prophylaxis for *Pneumocystis carinii* pneumonia (PCP) before and during PASSHIV-1 treatment. One of the patients suffering from widespread Kaposi's sarcoma had been on a cytostatic regimen of bleomycin, vincristine and adriamycin for 12 months without any effect on his sarcoma lesions. This patient had developed severe bone-marrow depression as a result of this regimen. Another patient had been receiving local injections of vinblastine into

TABLE 12

Characteristics of patients receiving PASSHIV-1 treatment.

| Patient | Age | Sex | Demographics | Route of infection | Walter Reed stage* |
|---------|-----|-----|--------------|--------------------|--------------------|
| First Cycle | | | | | |
| 1 | 44 | M | USA | ST | WR3 (C, B) |
| 2 | 48 | M | USA | ST | WR3 (C, B) |
| 3 | 33 | M | USA | IVDU | WR6 (C, B, KS) |
| 4 | 39 | M | Netherlands | ST | WR6 (C, B, CNS) |
| 5 | 23 | M | USA | ST | WR3 (C, B) |
| 6 | 48 | M | USA | ST | WR2 |
| 7 | 46 | M | USA | ST | WR5 |
| 8 | 44 | M | Netherlands | ST | WR6 (B, KS, CNS) |
| 9 | 39 | M | USA | ST | WR6 (C, B, KS, CNS) |
| 10 | 45 | M | USA | ST | WR5 (B, K) |
| 11 | 29 | F | USA | IVDU | WR2 |
| 12 | 30 | F | USA | ST | WR1 |
| 13 | 43 | M | USA | ST | WR6 (CNS) |
| 14 | 38 | M | USA | ST | WR4 (KS, CNS) |
| Second Cycle | | | | | |
| 1 | 44 | M | USA | ST | WR3 (C, B) |
| 5 | 23 | M | USA | ST | WR3 (C, B) |

*Clinical manifestations are shown in parentheses. M, male; F, female; ST, sexual transmission; IVDU, intravenous drug use; CNS, central nervous system involvement; C, candidiasis; B, bronchitis; KS, Kaposi's sarcoma.

Previous and concomitant therapy

Of the 14 patients who entered the PASSHIV-1 experimental protocol, five had been treated with high dose zidovudine (1200 mg per day) commencing in either 1987 or 1989, for 3 months to 3 years. All five had stopped this high-dose regimen because of side-effects; three were on 300–600 mg per day (low dose) during PASSHIV-1 treatment. In two of these patients the treatment regimen was changed to low-dose zidovudine combined with ddC or ddI 3–4 months before PASSHIV-1, with no apparent change in their general condition and with no effect on their CD4+ cell count.

Eight of the 14 patients commenced low-dose zidovudine (400–600 mg per day). Three discontinued zidovudine after <3 months because of side-effects, and commenced ddC and ddI, but had to discontinue treatment within 1–3 months, again because of side-effects. These three patients were not taking any therapy at the time of this trial. Three patients were started on a combination of low-dose zidovudine and ddC 3–12 months before PASSHIV-1 treatment. Two of these patients had side-effects during the treatment and his widespread Kaposi's sarcoma lesions without effect. One patient was on erythropoietin because of side-effects caused by zidovudin.

PASSHIV-1 immunotherapy trial

PASSHIV-1 intravenous infusion was performed in a controlled environment, with all necessary emergency equipment in place to treat possible hypersensitivity reactions. PASSHIV-1 was infused at a flow rate of 12 ml/h for the first 40–60 min. In the absence of side-effects, flow rate was increased to 60 ml/h. Vital signs were monitored every 15–30 min. The daily infusion took 4 h to complete. Patients were infused daily for 5–7 days with 2–3 g daily PASSHIV-1 diluted 1:5 in human albumin (Kabi-Pharmacia, Copenhagen, Denmark). The total dose of PASSHIV-1 administered was 10–14 g.

Following the initial hospitalization, patients were re-evaluated every 2 weeks for the first month following the initiation of therapy, and monthly thereafter. Each follow-up visit included clinical evaluation and complete blood count (CBC). General laboratory evaluation, including CBC and clinical chemistries, were obtained at 0, 1, 2 and 3 months.

All aspects of patient data collection were supervised by a clinical coordinator. Follow-up of these patients was at least 6 months following the first-cycle therapy, and at least 3 months following the second-cycle therapy.

Clinical and laboratory parameters

At each follow-up visit, patients were examined and questioned about their primary symptoms before institution of therapy and any additional symptoms that had arisen since the institution of therapy. Subjective symptoms, such as appetite and fatigue, were assessed using a visual analog scale (0–100 mm) three to five times during and after PASSHIV-1 treatment. Higher scores reflect positive symptoms such as increased appetite or increased energy, lower scores negative symptoms, such as fatigue and lack of appetite. BRUERA E., MACMILLAN K., KUEHN N., HANSON J., MACDONALD R. N.: A controlled trial of megestrol acetate on appetite, caloric intake, nutritional status, and other symptoms in patients with advanced cancer, Cancer 1990, 66:1279–1282. A change of $\geq 20$ mm on this scale was considered important (with normalization of the parameter indicating 100 mm for positive parameters or 0 mm for negative parameters). Chronic diarrhea was defined as an estimated excess of 200 cm$^3$ loose to watery stools daily for more than 1 month. Other clinical parameters, such as candidiasis or vaginitis, were based on physician assessment and patient history.

Laboratory parameters measured on admission included complete blood count, platelet count, and clinical chemistry profile Na, K, Cl, $CO_2$, blood urea nitrogen (BUN), creatinine, total protein, albumin, $Ca^{2+}$, AST, alanine aminotransferase, total bilirubin, alkaline phosphatase, and lactic dehydrogenase (LDH). These were repeated at each monthly follow-up visit for all parameters for 3 months. CD4+ counts were evaluated upon admission, before discharge, and at the 1- and 2-month follow-up visits. In some patients, CD4+ counts were also repeated at 3 or 4 months of follow-up. To assess both hematological and biochemistry values, the normal range used was based upon the 95% confidence interval (CI) of a healthy Danish population. Additional changes considered important are noted in the specific tables.

Results

Side-effects

Although porcine products are often well tolerated when administered to humans, they can elicit xenogeneic immune responses. All patients were therefore carefully screened for evidence of deleterious immune responses to the porcine immunoglobulin administered. Of 14 patients treated with PASSHIV-1 (first-cycle treatment), and the two patients retreated with PASSHIV-1 (second-cycle treatment), one developed serum sickness (hypersensitivity type 3) on day 12 after first-cycle treatment (total dose, 10 g). This patient was also the only one to receive human intravenous γ-globulin on day 5 of treatment with PASSHIV-1. Clinical manifestations were headache, fever, maculopapular rash and arthralgias. He was treated for 3–4 days with high doses of parenterally administered hydrocortisone and non-steroidal anti-inflammatory agent (NSAID). His platelet count decreased from a baseline of 173 to $124 \times 10^6$/l 3 days after cessation of PASSHIV-1 treatment. The platelet count increased 5 days after discharge and was within normal range 1–5 months post-treatment. No changes in CBC were noted. His blood biochemistry measurements, such as serum creatinine and BUN, remained within the normal range. Despite his hypersensitivity reaction, the patient's CD4+ cell count increased significantly from $112 \times 10^6$/l during treatment to $375 \times 10^6$/l approximately 1.5 months post-treatment (Table 13).

TABLE 13

CD4 cell response to (a) first-cycle and (b) second-cycle PASSHIV-1 therapy (cellular response to passive immunotherapy).

(a) First-cycle

| | CD4+ cell count ($\times 10^6$/l) | | | |
|---|---|---|---|---|
| Patient | Before | After | 2–3 months after | 4–6 months after |
| 1* | 113 | 82 | 425 | 410 |
| 2 | 22 | 13 | 43 | 20 |
| 3* | 16 | 12 | 70 | 43 |
| 4* | 5 | 8 | 13 | 50 |
| 5* | 13 | 10 | 48 | 80 |
| 6* | 205 | 222 | 260 | 490 |
| 7* | 112 | 120 | 220 | 375 |
| 8 | 9 | 8 | 10 | 8 |
| 9 | 14 | 5 | 16 | 12 |
| 10 | 15 | 7 | 11 | 11 |
| 11 | 945 | 907 | 1068 | 1058 |
| 12 | 467 | 483 | 490 | 663 |
| 13 | 63 | 14 | 76 | 55 |
| 14 | 0 | 10 | 10 | 0 |
| Mean ± s.d. | 143 ± 263 | 136 ± 259 | 197 ± 297 | 234 ± 323 |
| P value | | 0.208 | 0.030 | 0.013 |

(b) Second-cycle

| | CD4+ cell count ($\times 10^6$/l) | | |
|---|---|---|---|
| Patient | Before | After | <2 months after |
| 1* | 325 | 367 | 561 |
| 5 | 80 | 69 | 96 |

*Increase in CD4+ cells > 3 s.d. at 4–6 months following first-cycly or <2 months following second-cycle therapy.

Three patients developed minor urticarial rashes during or after treatment, all of whom responded to a single antihistamine injection. The cases with rash did not appear to be consistent with exposure to daily repeated PASSHIV-1 infusions, because in two of the cases the rash, consisting of a few urticarial elements, appeared on day 1 or day 2 of infusion and did not reappear, despite continuing daily infusions. One of these patients was retreated with PASSHIV-1 (second-cycle treatment) approximately 2.5 months after the first-cycle treatment and did not develop any urticaria during the second cycle. Follow-up of at least 3 months revealed no additional side-effects attributable to therapy.

Patient responses to treatment

Laboratory parameters

With the exception of the decrease in platelet numbers in one patient who developed serum sickness, the laboratory values and biochemistry of the patients treated did not appear to be adversely affected by the treatment. None of the patients with normal clinical chemistry values at initiation of therapy developed abnormalities in these parameters upon follow-up. Of seven patients with initially normal leukocyte counts, one had a count below normal at week 12. Seven patients initially had normal platelet counts: one (on concomitant zidovudine therapy) fell to below normal at week 12. Nine patients had initially normal hemoglobins: two (both were receiving concomitant zidovudine therapy) fell to below normal at week 12.

Figure 6:
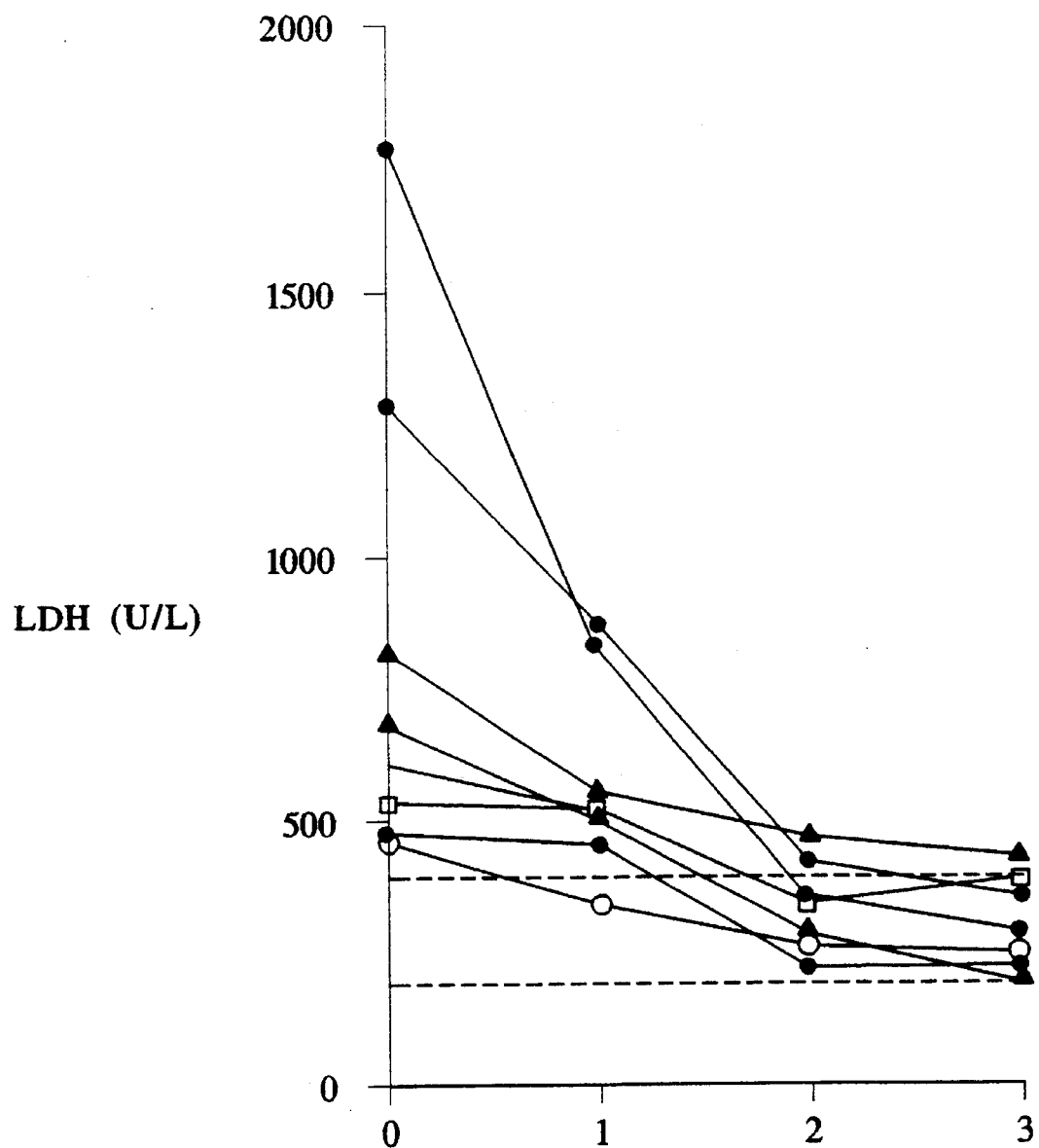
FIG. 6 is a diagram of lactate (LDH) activity in patients with initially abnormal values. Serum LDH is shown before therapy (0) and at weeks 2,4, and 12 post-therapy. Normal range ( - - - ).

Laboratory parameters that were abnormal before treatment were evaluated. Of seven patients with thrombocytopenia, five demonstrated >10% increases in their platelet counts following treatment, with three improving to normal values. Of five patients with anemia, two experienced >0.5 mmol/l increases in hemoglobin values at some time after therapy; one out of the five had sustained increase and achieved normal values. Of seven patients with leukopenia, three increased to normal range and two increased by >10%. Similarly, of nine patients with elevated LDH, eight decreased to normal values and one to near normal values (FIG. 6). Of three patients with elevated alkaline phosphatase, all decreased to normal values (FIG. 7). This PASSHIV-1 treatment could lead to improved cell bone-marrow production, and possibly liver function, as demonstrated by the normalizations of LDH and alkaline phosphatase.

All patients were followed for at least 7 months. CD4+ counts were obtained at the initiation of therapy, at the completion of therapy, 2–3 months and 4–6 months post-treatment (Table 13). CD4+ levels did not change significantly between the initiation of and immediately following therapy (mean CD4+counts were $142.8 \pm 262.9 \times 10^6/l$ before the initiation of therapy and $135.8 \pm 258.6 \times 10^6/l$ 2–3 months (mean, $197.1 \pm 297.3 \times 10^6/l$; P=0,030, paired Student's t-test) and 4–6 months post-therapy (mean, $233.9 \pm 323.0 \times 10^6/l$; P=0.013, paired Student's t-test).

Two patients were retreated with PASSHIV-1 (second-cycle) approximately 3 months after their first-cycle treatment (Table 13). CD4 cell count also increased after the second-cycle treatment.

Four of the patients treated with PASSHIV-1 were HIV-1 p24-core-antigen-positive before the first-cycle treatment. All four became HIV-1 p24-core-antigen-negative on day 3 of treatment, and remained p24-negative for at least 4 months following therapy. One was p24-negative before the initiation of second-cycle treatment with PASSHIV-1, and 3 months after both first- and second-cycle treatments. Ten patients were HIV-1 p24-core-antigen-negative before first-cycle treatment and remained negative throughout the observation period.

Clinical parameters

Parameters evaluated are summarized in Table 14. All patients showed an increase in appetite during treatment with PASSHIV-1. Eleven patients had over 10% weight loss before PASSHIV-1 treatment. Four of the 11 patients regained or exceeded their original weight (weight before the patient had any symptoms of HIV-1 infection); The remaining seven gained between 2.3 and 8.6 kg after treatment. Thus, PASSHIV-1 treatment had a 100% effect on weight gain in this group of patients.

Four patients who had frequent intermittent periods of fever lasting over 3 weeks, including three with night sweats, have not experienced fever or night sweats for >4 months, while episodes of diarrhea per day in the third have decreased from 25 before PASSHIV-1 treatment to 4–6 episodes per day. Two patients had widespread eczema-like dermatitis before treatment with PASSHIV-1. During the 4–6 month follow-up the dermatitis disappeared rapidly during the third or fourth treatment day and has not reappeared.

One of the female patients had frequent vaginal yeast infections, treated with fungistatic suppositories. Following PASSHIV-1 treatment, she has not experienced any reappearance of vaginal yeast infections and has not required fungistatic treatment. Three of the 14 patients had frequent (at least monthly) candidiasis that required antifungal antibiotic treatment. After treatment with PASSHIV-1, none of these patients had a reoccurrence of candidiasis during the 4–6-month follow-up period.

TABLE 14

Clinical effects of PASSHIV-1 treatment.

| Clinical parameter | Patients | Improved but not normalized | Normal-ized | No change | Worse |
|---|---|---|---|---|---|
| Fatigue | 11 | 0 | 11 | 0 | 0 |
| Night sweats | 3 | 0 | 3 | 0 | 0 |
| Weight loss | 11 | 7 | 4 | 0 | 0 |
| Diarrhea | 3 | 1 | 2 | 0 | 0 |
| Fever | 4 | 0 | 4 | 0 | 0 |
| Bronchitis | 4 | 0 | 4 | 0 | 0 |
| Dermatitis | 2 | 0 | 2 | 0 | 0 |
| Vaginal yeast infection | 1 | 0 | 1 | 0 | 0 |
| Candidiasis | 3 | 0 | 3 | 0 | 0 |
| Poly-neuropathy | 4 | 0 | 4 | 0 | 0 |
| Kaposi's sarcoma | 5 | 1 | 0 | 4 | 0 |

Symptoms were considered present acccording to the following criteria: fatigue, <90% on visual analog scale of energy; night sweats, present or absent based on history; weight loss, decrease by >10% from weight prior to onset of symptoms; diarrhea, >200 cc/day for >1 month; fever, temperature >38° C. intermittant for >3 weeks; bronchitis, episodes requiring antibiotic therapy at least monthly for >1 year; dermatitis, present chronically for >1 month; vaginal yeast infection; present monthly requiring antifungal therapy for >6 months; candidiasis, recurrences at least monthly for >6 months; polyneuropathy, chronically present, confirmed by a physician for >3 months; Kaposi's sarcoma, biopsy-proven lesions. Normalization indicates return of parameters to status prior to development of AIDS. Improvement without normalization was considered as follows: weight loss, increase by >2.3 kg pretreatment weight; diarrhea, decrease by >50% in stool volume per week; Kaposi's sarcoma, decrease by >50% in size of lesions.

Four patients had polyneuropathy with severe neurological symptoms in their lower extremities, often with severe bone pains in their legs, over a period ranging from 6 to 14 months. Two of the patients were minimally ambulatory because of lower extremity numbness, and one was wheelchair-bound. All patients reported significant relief from their neurological symptoms by day 3 of treatment, and their neurological symptoms and pains disappeared during or at the end of PASSHIV-1 treatment. The three patients having difficulty ambulating, including the patient in the wheelchair, were able to walk for long distances 5–12 days after the initiation of treatment. It will be important to further evaluate this unexpected result in a larger patient population.

Five of the patients had PCP prior to their admission for PASSHIV-1 treatment. Although none has relapsed since treatment, the follow-up period of 3–6 months is too short to evaluate the effect of the treatment in improving PCP symptoms. Furthermore, all five patients were continued on prophylactic antibiotic treatment. Four patients had chronic bronchitis that required frequent antibiotic therapy before treatment with PASSHIV-1; none has had bronchitis since PASSHIV-1 treatment or required antibiotic treatment during the last 3–6 months of follow-up.

Of 14 patients treated with PASSHIV-1, seven had CD4 cell counts $<20 \times 10^6/l$ at the start of treatment. Five of these patients had Kaposi's sarcoma. One showed a partial response after PASSHIV-1 therapy, demonstrated by a 50% decrease in tumor size in three out of three sarcoma lesions. Another responded with an in increase in CD4+ cell count from <20 to $70 \times 10^6/l$, concomitant with a transient minor response in the size of some of his widespread sarcoma lesions, especially those located on the lower extremities. The antitumor response lasted for approximately 1 month, but was minimal at best.

Patient perspective

Only one of the patients did not requested retreatment. All other patients treated with first-cycle treatment of PASSHIV-1 have voluntarily requested in writing that they be retreated (second-cycle treatment with PASSHIV-1).

From this study, we conclude that PASSHIV-1 can be administered safely to patients with HIV-1 infection, regardless of clinical status. While additional side-effects may be encountered as more individuals are treated with this therapy, the toxicity in this study was low. The encouraging clinical and laboratory response seen in this trial suggests that continued study of the efficacy of PASSHIV-1 in the treatment of HIV-1 infection is warranted.

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for maintaining CD4+ cell counts in a healthy patient, or increasing CD4+ cell counts in a patient infected by HIV comprising administering in a pharmaceutically acceptable carrier an effective amount of a porcine hyper-immune serum said hyper-immune serum containing polyclonal anti-gp48 antibodies among other antibodies, and said hyper-immune serum is produced by the immunization of a pig with HIV vital lysate which contains gp48 protein.

* * * * *

UNITED STATES PATENT AND TRADEMARK OFFICE
CERTIFICATE OF CORRECTION

PATENT NO. : 5,529,776
DATED : June 25, 1996
INVENTOR(S) : Osther et al.

It is certified that error appears in the above-indentified patent and that said Letters Patent is hereby corrected as shown below:

At column 40, line 12

The word "vital" should read - -viral - -

Signed and Sealed this

Thirty-first Day of December, 1996

*Attest:*

BRUCE LEHMAN

*Attesting Officer*     *Commissioner of Patents and Trademarks*